(12) United States Patent  (10) Patent No.: US 9,019,425 B2
Senda et al.  (45) Date of Patent: Apr. 28, 2015

(54) IMAGE PICKUP UNIT AND IMAGE PICKUP DISPLAY SYSTEM

(71) Applicant: Sony Corporation, Tokyo (JP)

(72) Inventors: Michiru Senda, Kanagawa (JP); Yasuhiro Yamada, Kanagawa (JP)

(73) Assignee: Sony Corporation, Tokyo (JP)

( * ) Notice: Subject to any disclaimer, the term of this patent is extended or adjusted under 35 U.S.C. 154(b) by 46 days.

(21) Appl. No.: 13/650,328

(22) Filed: Oct. 12, 2012

(65) Prior Publication Data

US 2013/0100302 A1 Apr. 25, 2013

(30) Foreign Application Priority Data

Oct. 19, 2011 (JP) .................................. 2011-229996

(51) Int. Cl.
- H04N 5/235 (2006.01)
- H04N 5/225 (2006.01)
- H04N 5/32 (2006.01)
- H04N 5/359 (2011.01)
- H04N 5/378 (2011.01)
- A61B 6/00 (2006.01)

(52) U.S. Cl.
CPC .................. *H04N 5/32* (2013.01); *H04N 5/359* (2013.01); *H04N 5/378* (2013.01); *A61B 6/4233* (2013.01)

(58) Field of Classification Search
CPC ............................ H04N 5/335; H04N 5/35572
USPC ........................................ 348/208.1, 308, 362
See application file for complete search history.

(56) References Cited

U.S. PATENT DOCUMENTS

| 8,009,224 | B2 * | 8/2011 | Umeda .......................... 348/362 |
| 8,014,187 | B2 * | 9/2011 | Kang et al. ..................... 365/148 |
| 8,582,010 | B2 * | 11/2013 | Cieslinski et al. ............. 348/308 |
| 2006/0180774 | A1 * | 8/2006 | Endo ............................ 250/485.1 |
| 2008/0151091 | A1 * | 6/2008 | Hynecek ........................ 348/308 |
| 2010/0020594 | A1 * | 1/2010 | De Sandre et al. ........... 365/163 |
| 2013/0093927 | A1 | 4/2013 | Yamada |
| 2013/0100327 | A1 | 4/2013 | Senda et al. |

FOREIGN PATENT DOCUMENTS

JP 2001-135561 A 7/2011

* cited by examiner

*Primary Examiner* — Trung Diep

(74) *Attorney, Agent, or Firm* — Wolf, Greenfield & Sacks, P.C.

(57) ABSTRACT

An image pickup unit includes: an image pickup section having a plurality of pixels each including a photoelectric conversion device and a field effect transistor; and a driving section, by using the transistor, that executes read driving and reset driving on a signal charge stored in the pixel. The driving section intermittently executes the reset driving a plurality of times in a one-frame term, and executes on-operation of the transistor by applying, to the transistor over at least one resetting term in the one-frame term or over a partial term in the at least one resetting term, a second voltage that is lower than a first voltage applied in a resetting term in the one-frame term other than the at least one resetting term.

12 Claims, 29 Drawing Sheets

JUST AFTER END OF Tr1
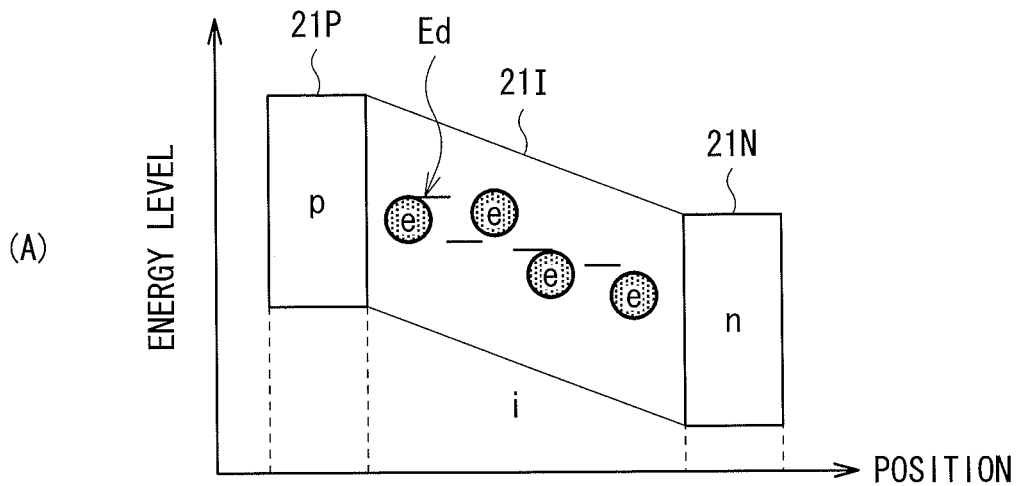
AFTER PREDETERMINED TIME HAS ELAPSED FROM Tr1
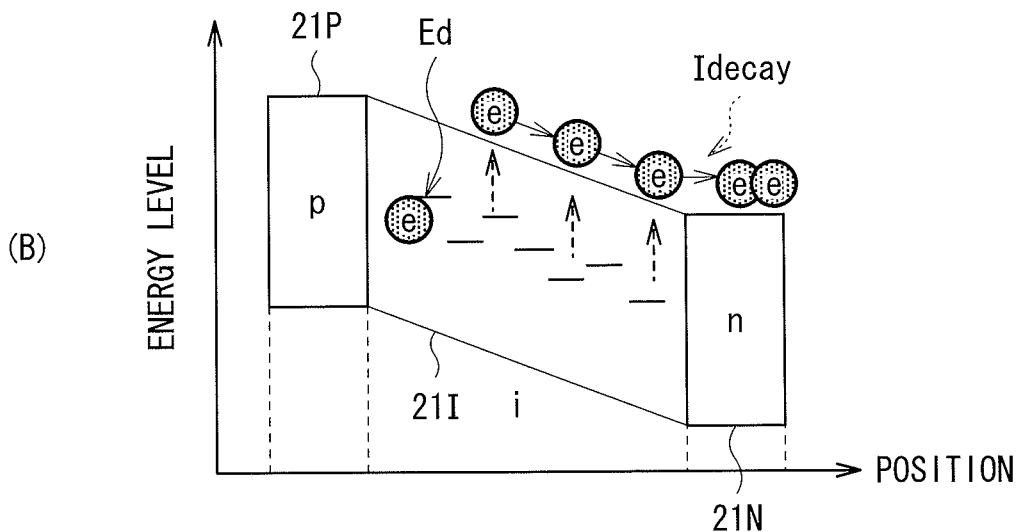
F I G. 10

SECOND RESETTING TERM Tr2 (FIRST OPERATIONAL EXAMPLE)

SECOND RESETTING TERM Tr2 (SECOND OPERATIONAL EXAMPLE)

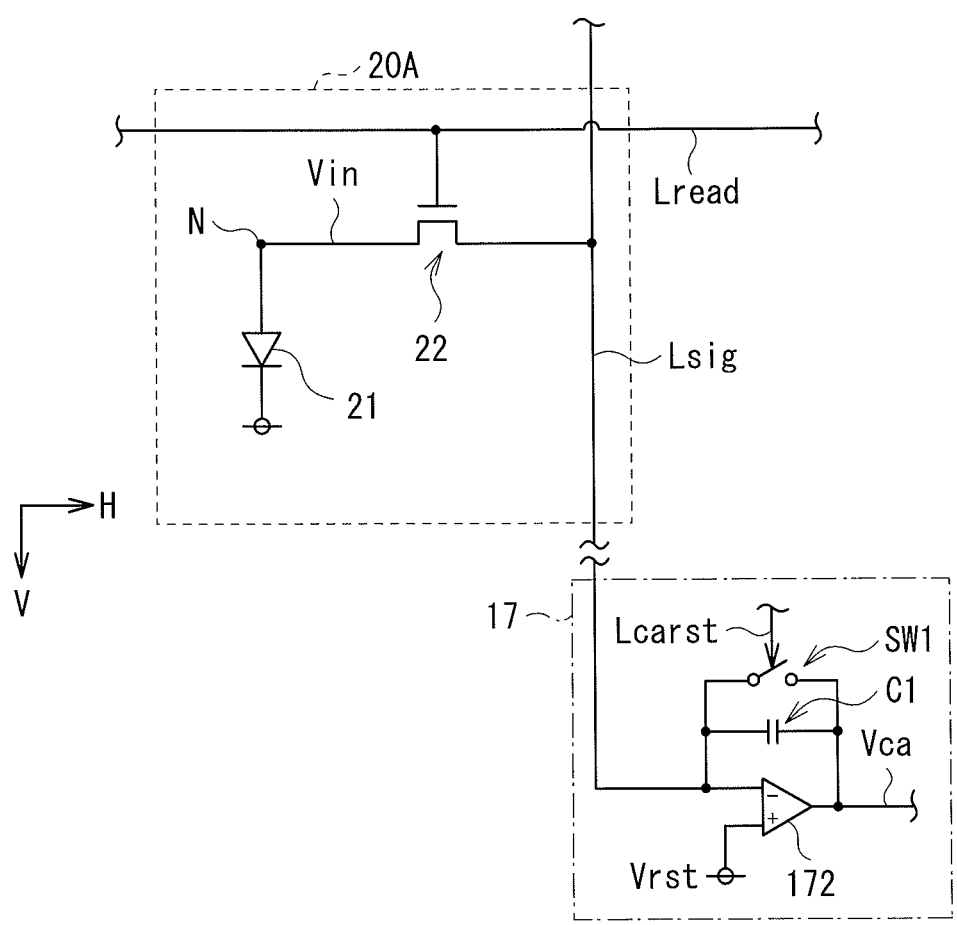
F I G. 25

IMAGE PICKUP UNIT AND IMAGE PICKUP DISPLAY SYSTEM

CROSS REFERENCE TO RELATED APPLICATIONS

The presented application claims priority under 35 U.S.C. §119 to Japanese Patent Application. No. JP 2011-229996, filed in the Japan Patent Office on Oct. 19, 2011, the entire contents of which are incorporated herein by reference.

BACKGROUND

The present disclosure relates to an image pickup unit that includes a photoelectric conversion device, and an image pickup display system that includes the image pickup unit.

Various types of image pickup units are proposed as an image pickup unit of the type that an photoelectric conversion device is built into each pixel (an image pickup pixel) nowadays. As examples of the image pickup unit that includes a photoelectric conversion device as mentioned above, for example, a so-called optical touch panel, a radioactive image pickup unit, and the like may be given (see, for example, Japanese Unexamined Patent Application Publication No. 2011-135561).

Although, in general, image pickup data is obtained by performing signal charge read driving and reset driving on a plurality of pixels in an image pickup unit as mentioned above, it has such an issue that noise generates in an output signal caused by the reset driving so performed to thereby deteriorate the image quality of a picked-up image.

SUMMARY

It is desirable to provide an image pickup unit capable of increasing image quality of a picked-up image, and an image pickup display system that includes the image pickup unit.

An image pickup unit according to an embodiment of the present disclosure includes: an image pickup section having a plurality of pixels each including a photoelectric conversion device and a field effect transistor; and a driving section, by using the transistor, executing read driving and reset driving on a signal charge stored in the pixel. The driving section intermittently executes the reset driving a plurality of times in a one-frame term, and executes on-operation of the transistor by applying, to the transistor over at least one resetting term in the one-frame term or over a partial term in the at least one resetting term, a second voltage that is lower than a first voltage applied in a resetting term in the one-frame term other than the at least one resetting term.

An image pickup display system according to an embodiment of the present disclosure is provided with an image pickup unit and a display. The display displays an image based on an image pickup signal obtained from the image pickup unit. The image pickup unit includes: an image pickup section having a plurality of pixels each including a photoelectric conversion device and a field effect transistor; and a driving section, by using the transistor, executing read driving and reset driving on a signal charge stored in the pixel. The driving section intermittently executes the reset driving a plurality of times in a one-frame term, and executes on-operation of the transistor by applying, to the transistor over at least one resetting term in the one-frame term or over a partial term in the at least one resetting term, a second voltage that is lower than a first voltage applied in a resetting term in the one-frame term other than the at least one resetting term.

In the image pickup unit and the image pickup display system according to the above-described respective embodiments of the present disclosure, photoelectric conversion based on incident light is performed in each of the pixels of the image pickup section, and the read driving and the reset driving of the signal charge are performed, by which a picked-up image based on the incident light is obtained. The driving section intermittently performs the reset driving a plurality of times in the one-frame term, and applies, to the transistor over at least one resetting term in the one-frame term or over the partial term in the at least one resetting term, the second voltage that is lower than the first voltage applied in the resetting term in the one-frame term other than the at least one resetting term. Thus, it is allowed to reduce so-called charge injection which would occur by switching from ON operation to OFF operation of the transistor in execution of the reset driving.

According to the image pickup unit and the image pickup display system of the above-described respective embodiments of the present disclosure, each of the pixels of the image pickup section includes the photoelectric conversion device, and the driving section performs the read driving and the reset driving of the signal charge from each of the pixels, by which it is allowed to obtain the picked-up image which is based on the incident light. The driving section performs the reset driving the plurality of times, and applies, to the transistor over at least one resetting term in the one-frame term or over the partial term in the at least one resetting term, the second voltage that is lower than the first voltage applied in the resetting term in the one-frame term other than the at least one resetting term. Thus, it is allowed to reduce charge injection which would occur in association with execution of the resetting operation. Hence, it is allowed to increase image quality of the picked-up image.

It is to be understood that both the foregoing general description and the following detailed description are exemplary, and are intended to provide further explanation of the technology as claimed.

BRIEF DESCRIPTION OF THE DRAWINGS

The accompanying drawings are included to provide a further understanding of the disclosure, and are incorporated in and constitute a part of this specification. The drawings illustrate embodiments and, together with the specification, serve to explain the principles of the technology.

FIG. 10 is a characteristic diagram illustrating an example of a mechanism of signal charge residue.

FIG. 25 is a circuit diagram illustrating a configuration example of a pixel and the like according to a modification example 2.

DETAILED DESCRIPTION

Next, preferred embodiments of the present disclosure will be described in detail with reference to the accompanying drawings. It is to be noted that description will be made in the following order.
1. Embodiment (an example of an image pickup unit that performs an image picking-up operation by making a gate voltage which is applied in execution of second reset driving lower than that applied in execution of first reset driving)
2. Modification Example 1 (an example in which the gate voltage which is applied in execution of the second reset driving is stepwise lowered)
3. Modification Example 2 (one example of a passive type pixel circuit)
4. Modification Example 3 (another example of the passive type pixel circuit)
5. Modification Examples 4 and 5 (examples of an active type pixel circuit)
6. Modification Example 6 and 7 (examples of an image pickup section that performs an image picking-up operation on the basis of radioactive rays)
7. Application Example (an example applied to an image pickup display system)

EMBODIMENT

General Configuration of Image Pickup Unit 1

Figure 1:
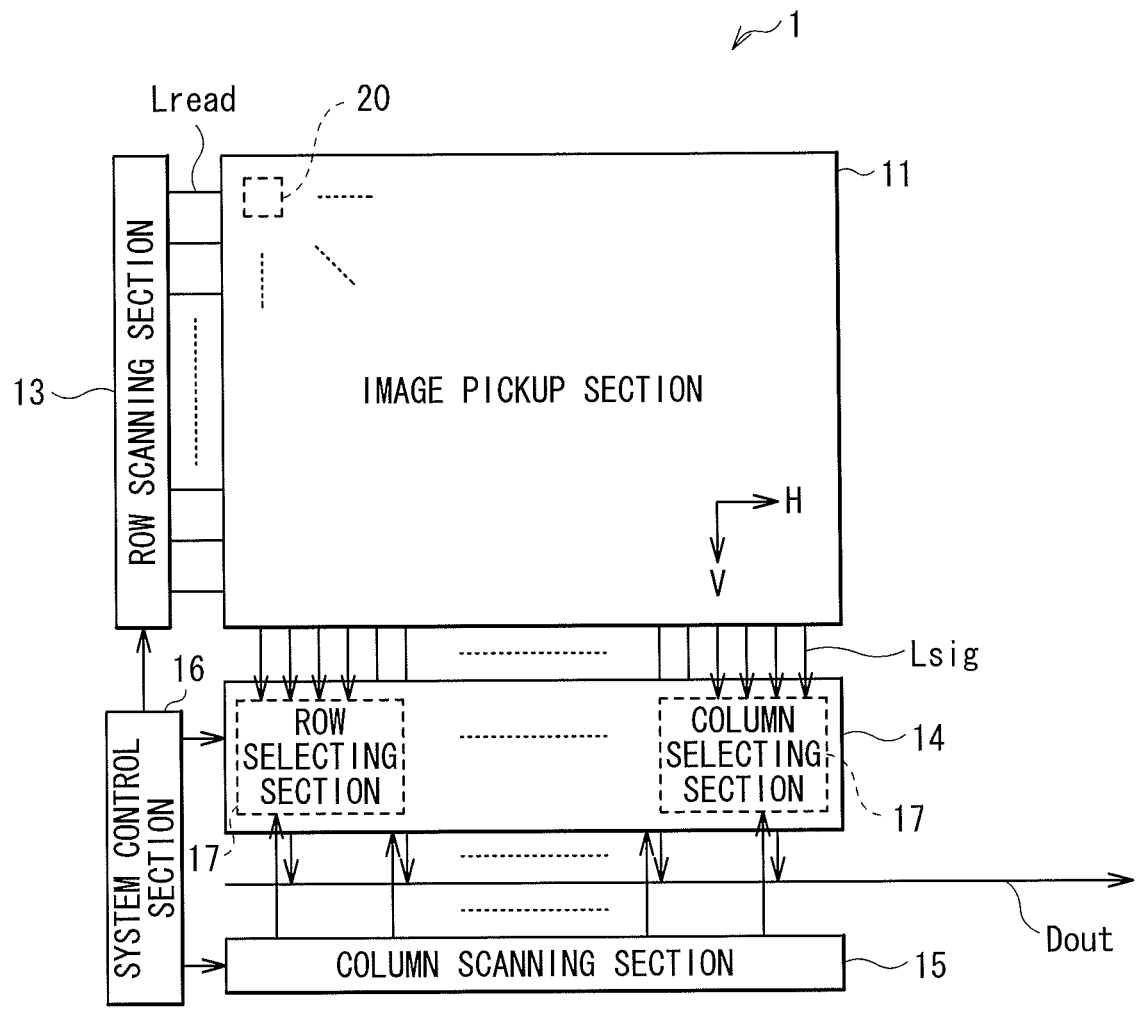
FIG. 1 is a block diagram illustrating a general configuration example of an image pickup unit according to an embodiment of the present disclosure.

FIG. 1 illustrates an example of a general block configuration of an image pickup unit (the image pickup unit 1) according to an embodiment of the present disclosure. The image pickup unit 1 reads information of an object (picks up an image of the object) on the basis of incident light (image pickup light). The image pickup unit 1 includes an image pickup section 11, a row scanning section 13, an A/D converting section 14, a column scanning section 15, and a system control section 16. The row scanning section 13, the A/D converting section 14, the column scanning section 15, and the system control section 16 in the above-mentioned sections correspond to a specific but not limitative example of the "driving section" in one embodiment of the present disclosure.

(Image Pickup Section 11)

The image pickup section 11 generates an electric signal in accordance with the incident light (the image pickup light). In the image pickup section 11, pixels 20 (image pickup pixels) 20 are two-dimensionally arranged in rows and columns (in a matrix). Each pixel 20 includes a photoelectric conversion device (a photoelectric conversion device 21 which will be described later) that generates photo-charges of a charge amount corresponding to the light quantity of the image pickup light and stores them therein. It is to be noted that, in the following, description will be made by referring a horizontal direction (a row direction) within the image pickup section 11 to as an "H" direction and referring a vertical direction (a column direction) to as a "V" direction as illustrated in FIG. 1.

Figure 2:
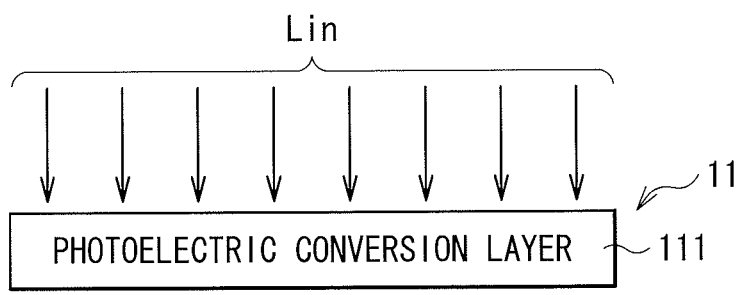
FIG. 2 is a schematic diagram illustrating a rough configuration example of an image pickup section illustrated in FIG. 1.

FIG. 2 illustrates a rough configuration example of the image pickup section 11. The image pickup section 11 includes a photoelectric conversion layer 111 on which photoelectric conversion devices 21 are arranged for the respective pixels 20. The photoelectric conversion layer 111 is configured such that photoelectric conversion (conversion from image pickup light Lin into a signal charge) which is based on the incident image pickup light Lin is performed as illustrated in FIG. 2.

Figure 3:
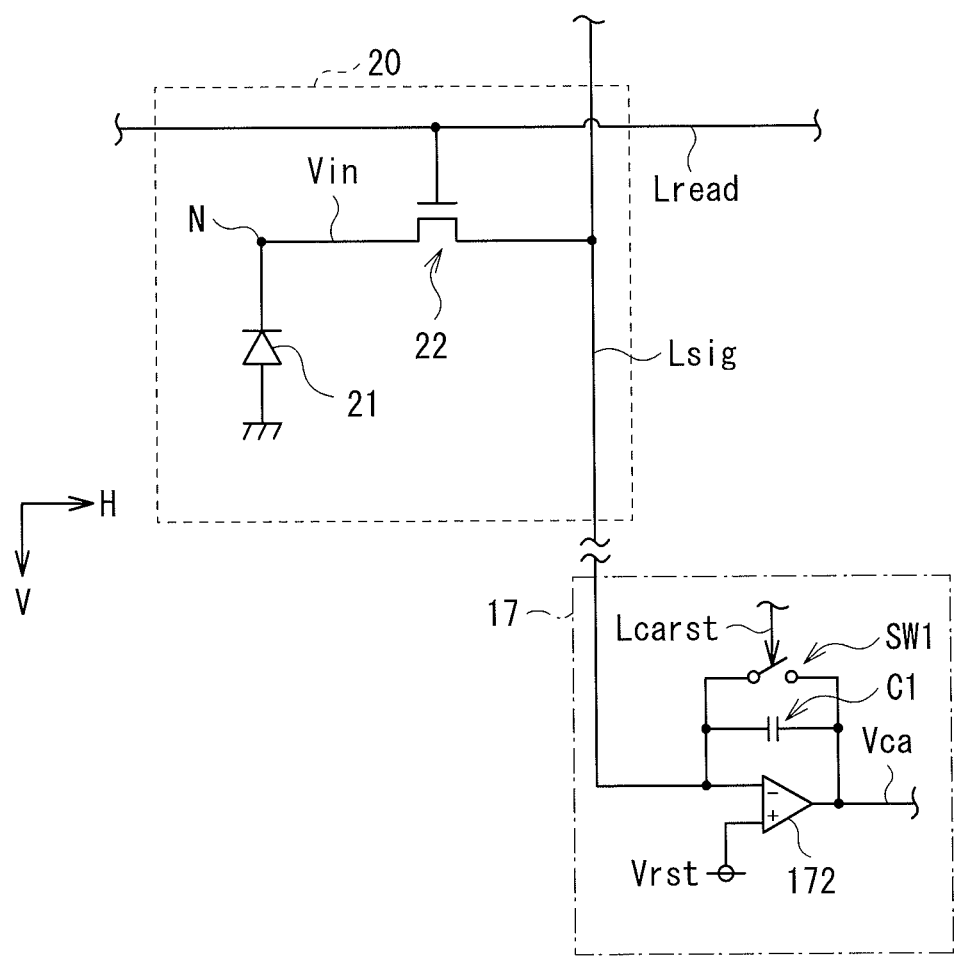
FIG. 3 is a circuit diagram illustrating a detailed configuration example of a pixel and the like illustrated in FIG. 1.

FIG. 3 illustrates an example of a circuit configuration (a so-called passive type circuit configuration) of the pixel 20 together with an example of a circuit configuration of a later-described row selecting section 17 included in the A/D converting section 14. The passive type pixel 20 includes one photoelectric conversion device 21 and one transistor 22. In addition, a read control line Lread extending in the H direction and a signal line Lsig extending in the V direction are connected to the pixel 20.

The photoelectric conversion device 21 is, for example, a PIN (Positive Intrinsic Negative) type photodiode or a MIS (Metal-Insulator-Semiconductor) type sensor, and generates signal charges of the charge amount corresponding to the light quantity of the incident light (the image pickup light Lin). It is to be noted that a cathode of the photoelectric conversion device 21 is connected to a storage node N in this example.

The transistor 22 is a transistor (a transistor for reading) that enters an on-state in accordance with a row scan signal which is supplied from the read control line Lread, to output the signal charge (an input voltage Vin) obtained from the photoelectric conversion device 21 to the signal line Lsig. Here, the transistor 22 is an N channel type (N-type) field effect transistor (FET). Alternatively, the transistor 22 may be a P channel type (P-type) FET or the like. In addition, the transistor 22 is configured by a silicon-based semiconductor such as, for example, non-crystalline silicon (amorphous silicon), microcrystalline silicon, and polycrystalline silicon (poly-silicon). Alternatively, it may be configured by an oxide semiconductor such as, for example, indium gallium zinc oxide (InGaZnO) and, zinc oxide (ZnO). In a circuit configuration of the pixel 20, a gate of the transistor 22 is connected to the read control line Lread, a source thereof is connected to, for example, the signal line Lsig, and a drain thereof is connected to, for example, a cathode of the photoelectric conversion device 21 via the storage node N. An anode of the photoelectric conversion device 21 is connected to ground (grounded) here. The present embodiment is configured to switchingly apply a two-valued (that is, later-described on-state potentials Von1 and Von2) on-state potential and an off-state voltage (an off-state voltage Voff) to the gate of the transistor 22 as a gate pulse. A voltage switching operation as mentioned above is implemented by, for example, buffer circuits 135A and 135B which will be described later.

(Row Scanning Section 13)

The row scanning section 13 is a pixel driving section (a row scan circuit) that includes a shift register circuit, predetermined logic circuits, and the like which will be described later, to perform row-by-row (in units of horizontal lines) driving (line sequential scanning) on the plurality of pixels 20 in the image pickup section 11. Specifically, it performs later-described image picking-up operations such as a reading operation, a resetting operation and the like, for example, by line sequential scanning. It is to be noted that the line sequential scanning is performed by supplying the above-mentioned row scan signal to each pixel 20 via the read control line Lread.

Figure 4:
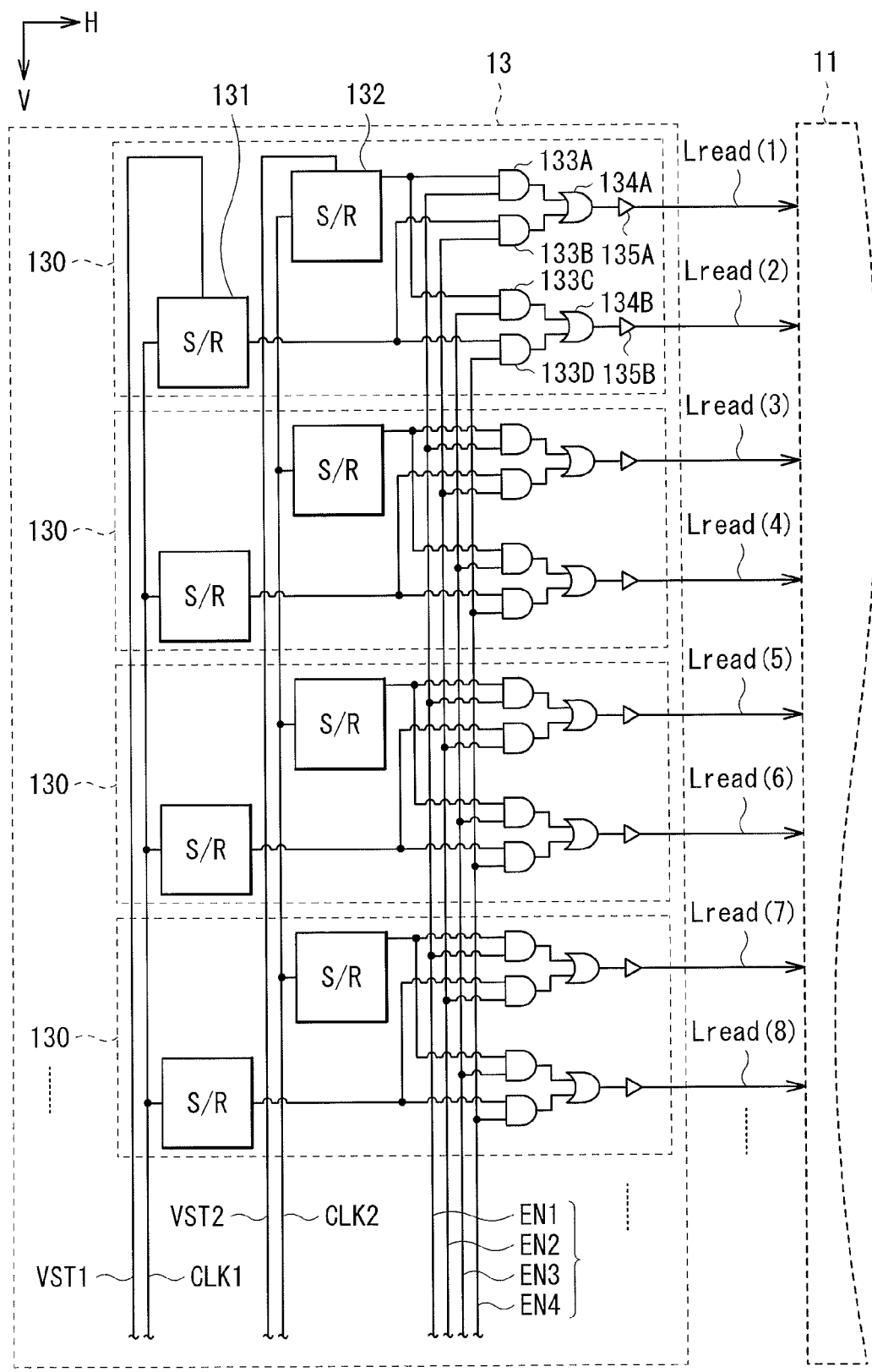
FIG. 4 is a block diagram illustrating a detailed configuration example of a row scanning section illustrated in FIG. 1.

FIG. 4 illustrates a block configuration example of the row scanning section 13. The row scanning section 13 includes a plurality of unit circuits 130 which are arrayed in the V direction. It is to be noted that the eight read control lines Lread which are connected to the four unit circuits 130 illustrated in FIG. 4 are designated by Lread (1) to Lread (8) in descending order here.

Each unit circuit 130 includes a plurality of columns (two columns in this example) of shift register circuits 131 and 132 (indicated as "S/R" for convenience' shake in the block: the same shall apply hereinafter), four AND circuits (logical product circuits) 133A to 133D, two OR circuits (logical sum circuits) 134A and 134B, and the two buffer circuits 135A and 135B.

The shift register circuit 131 is a circuit that generates a pulse signal used for sequentially shifting the plurality of unit circuits 130 as a whole in the V direction on the basis of a start pulse VST1 and a clock signal CLK1 supplied from the system control section 16. Similarly, the shift register circuit 132 is a circuit that generates a pulse signal used for sequentially shifting the plurality of unit circuits 130 as a whole in the V direction on the basis of a start pulse VST2 and a clock signal CLK2 supplied from the system control section 16. These shift register circuits 131 and 132 are disposed corresponding to the number of times (for example, two times) that later-described reset driving is executed (these circuits are disposed in two columns corresponding to the number of times executed). That is, for example, the shift register circuit 131 is in charge of generating a pulse signal used for executing the first reset driving and the shift register circuit 132 is in charge of generating a pulse signal used for executing the second reset driving.

Four kinds of enable signals EN1 to EN4 for controlling (defining) validity terms of the respective pulse signals (respective output signals) output from the shift register circuits 131 and 132 are input into the respective AND circuits 133A to 133D. Specifically, the pulse signal is input into one input terminal of the AND circuit 133A from the shift register circuit 132 and the enable signal EN1 is input into the other input terminal thereof. The pulse signal is input into one input terminal of the AND circuit 133B from the shift register 131 and the enable signal EN2 is input into the other input terminal thereof. The pulse signal is input into one input terminal of the AND circuit 133C from the shift register 132 and the enable signal EN3 is input into the other input terminal thereof. The pulse signal is input into one input terminal of the AND circuit 133D from the shift register 131 and the enable signal EN4 is input into the other input terminal thereof.

The OR circuit 134A is a circuit that generates a logical sum signal (an OR signal) of an output signal from the AND circuit 133A and an output signal from the AND circuit 133B. Similarly, the OR circuit 134B is a circuit that generates a logical sum signal of an output signal from the AND circuit 133C and an output signal from the AND circuit 133D. A logical sum signal of output signals (the pulse signals) output from the shift register circuits 131 and 132 is generated by the above-mentioned AND circuits 133A to 133D and the OR circuits 134A and 134B in the above-mentioned manner while controlling the validity terms of the respective output signals. Thus, driving timings and the like at which later-described reset driving is executed a plurality of times are defined.

The buffer circuit 135A is a circuit that functions as a buffer for the output signal (the pulse signal) from the OR circuit 134A, and the buffer circuit 135B is a circuit that functions as a buffer for the output signal from the OR circuit 134B. Pulse signals (row scan signals) so buffered by these buffer circuits 135A and 135B are output to each pixel 20 in the image pickup section 11 via the read control line Lread.

Figure 5A:
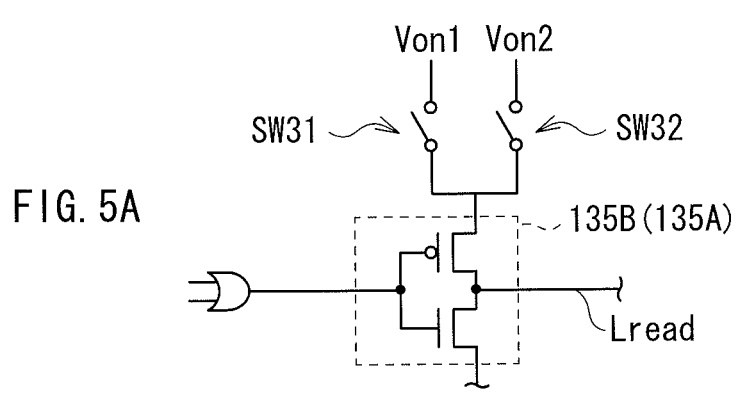
FIG. 5A and FIG. 5B are sectional diagrams illustrating configuration examples of a buffer circuit illustrated in FIG. 4.
Figure 5B:
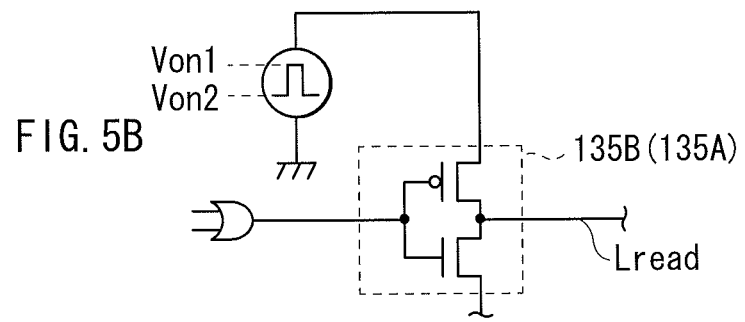

FIG. 5A and FIG. 5B are circuit diagrams illustrating examples of the buffer circuit 135A (135B). Although the on-state potentials Von1 and Von2 of the two-valued on-state potential are switchably applied to the read control line Lread as described above, a voltage switching operation as mentioned above may be implemented by a configuration using switches (switches SW31 and SW32), for example, as illustrated in FIG. 5A. Specifically, the switches SW31 and SW32 are disposed on the high side of the buffer circuit 135A (135B), the switch SW31 is held in an on-state, and the switch SW32 is held in an off-state, by which the high side is switched to the on-state potential Von1. On the other hand, the high side is switched to the on-state potential Von2 by holding the switch SW31 in the off-state and holding the switch SW32 in the on-state. Alternatively, a two-valued (Von1 and Von2) voltage pulse may be formed on the outside of the image pickup unit 1 to be used as a high-side voltage.

(A/D Converting Section 14)

The A/D converting section 14 includes a plurality of column selecting sections 17 which are prepared one by one for every plurality (here, four lines) of signal lines Lsig, and performs A/D conversion (analog/digital conversion) on the basis of a signal voltage (a signal charge) input via the signal line Lsig. Thus, output data Dout (an image pickup signal) which is in the form of a digital signal is generated and output to the outside.

Figure 6:
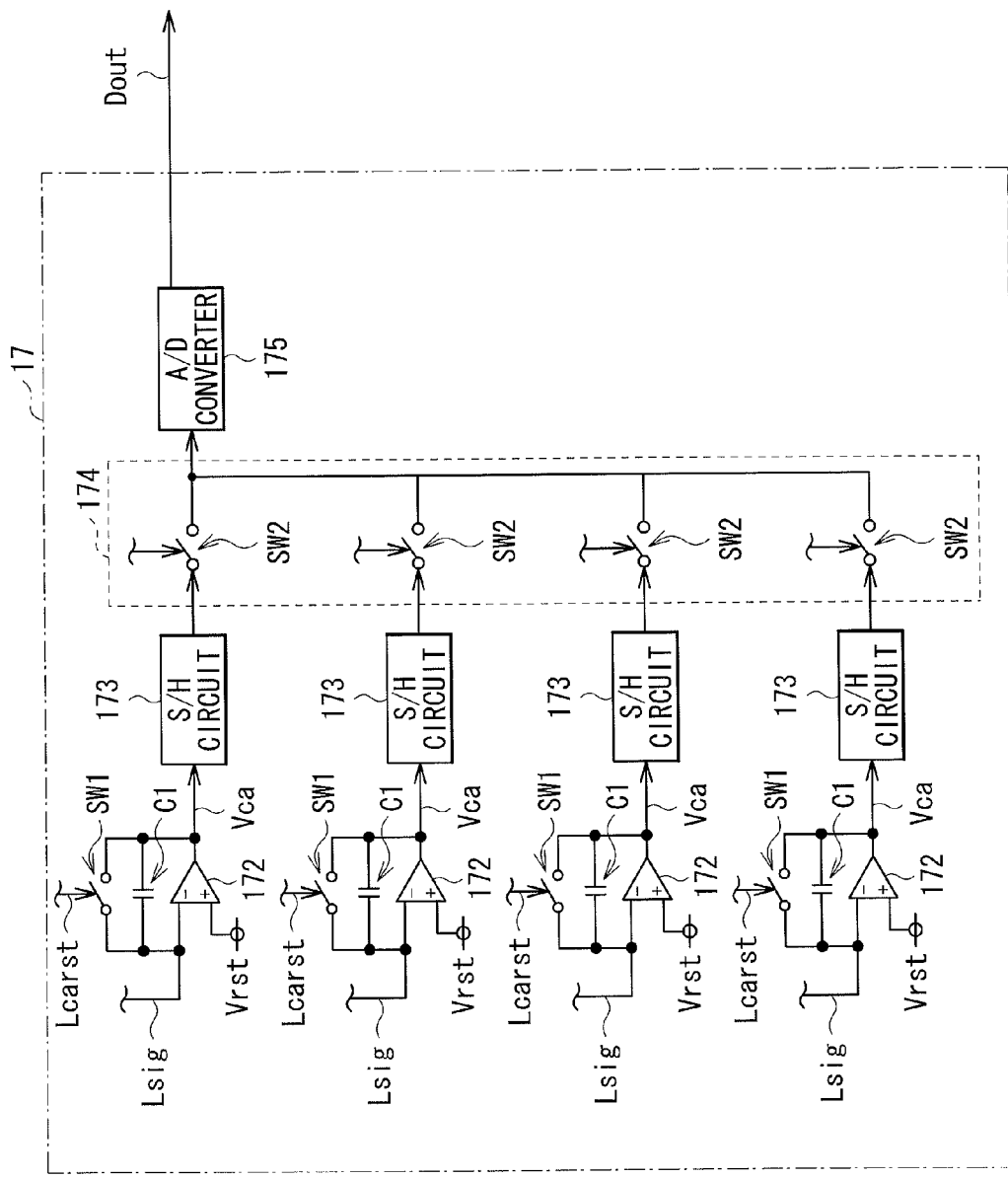
FIG. 6 is a block diagram illustrating a detailed configuration example of a column selecting section illustrated in FIG. 1.

Each column selecting section 17 includes a charge amplifier 172, a capacitative element (such as, for example, a capacitor, a feedback capacitative element, or the like) C1, a switch SW1, sample and hold (S/H) circuit 173, a multiplexer circuit (a selection circuit) 174 that includes four switches SW2, and an A/D converter 175, for example, as illustrated in FIG. 3 and FIG. 6, in which the charge amplifier 172, the capacitative element C1, the switch SW1, the S/H circuit 173, and the switches SW2 are prepared for each signal line Lsig, and the multiplexer circuit 174 and the A/D converter 175 are prepared for each column selecting section 17.

The charge amplifier 172 is an amplifier adapted to convert (Q-V convert) a signal charge read out from the signal line Lsig into a voltage. In the charge amplifier 172, a first end of the signal line Lsig is connected to a negative-side (minus-side) input terminal, and a predetermined reset voltage Vrst is input into a positive-side (plus-side) input terminal. An output terminal and the negative-side input terminal of the charge amplifier 172 are feedback-connected via a parallel connection circuit that includes the capacitative element C1 and the switch SW1. That is, one terminal of the capacitative element C1 is connected to the negative-side input terminal of the charge amplifier 172, and the other terminal thereof is connected to the output terminal of the charge amplifier 172. Similarly, one terminal of the switch SW1 is connected to the negative-side input terminal of the charge amplifier 172, and the other terminal thereof is connected to the output terminal of the charge amplifier 172. It is to be noted that the on/off state of the switch SW1 is controlled with a control signal (an amplifier reset control signal) which is supplied from the system control section 16 via an amplifier reset control line Lcarst.

The S/H circuit 173 is a circuit which is disposed between the charge amplifier 172 and the multiplexer circuit 174 (the switch SW2), to temporarily hold an output voltage Vca from the charge amplifier 172.

The multiplexer circuit 174 is a circuit in which four switches SW2 enter the on-states one after another in accordance with scan driving by the column scanning section 15, to selectively connect or disconnect each S/H circuit 173 with or from the A/D converter 175.

The A/D converter 175 is a circuit that generates and outputs the above-mentioned output data Dout by performing A/D conversion on an output voltage which is input from each S/H circuit 173 via each switch SW2.

(Column Scanning Section 15)

The column scanning section 15 includes, for example, a shift register, an address decoder, and the like which are not illustrated in the drawing, and drives in turn the respective switches SW2 in the above-mentioned column selecting section 17 while scanning them. Signals (the above-mentioned output data Dout) of the respective pixels 20 which are read out via the respective signal lines Lsig are output to the outside in turn by selective scanning performed by the column scanning section 15 so configured.

(System Control Section 16)

The system control section 16 controls the operations of the row scanning section 13, the A/D converting section 14, and the column scanning section 15. Specifically, the system control section 16 includes a timing generator that generates the above-mentioned various kinds of timing signals (the control signals), and controls to drive the row scanning section 13, the A/D converting section 14, and the column scanning section 15 on the basis of various timing signals so generated by the timing generator. The row scanning section 13, the A/D converting section 14, and the column scanning section 15 respectively perform image pickup driving (line sequential image pickup driving) on the plurality of pixels 20 in the image pickup section 11 under the control of the system control section 16 to acquire the output data D out from the image pickup section 11.

[Operations and Effects of Image Pickup Unit 1]

In the image pickup unit 1 according to the present embodiment, when the image pickup light Lin is incident on the image pickup section 11, the image pickup light Lin is converted (photoelectric-converted) into the signal charge by the photoelectric conversion device 21 in each pixel 20. In the above-mentioned occasion, a voltage change corresponding to the node capacity occurs at the storage node N due to storage of signal charges generated by photoelectric conversion. Specifically, assuming that Cs is a storage node capacity and q is a generated signal charge, the voltage changes (here, drops) by the amount of (q/Cs) at the storage node N. An input voltage Vin (corresponding to the signal charge) is applied to the drain of the transistor 22 in accordance with the voltage change as described above. When the input voltage Vin is supplied to the transistor 22 and the transistor 22 enters the on-sate in accordance with the row scan signal which is supplied from the read control line Lread, the signal charge stored in the storage node N is read out from each pixel 20 to the signal line Lsig.

The signal charges so read are input into the column selecting section 17 in the A/D converting section 14 via the signal lines Lsig in units of a plurality of columns (here, four columns) of pixels. In the column selecting section 17, first, Q-V conversion (conversion from a signal charge into a signal voltage) is performed on each signal charge input via each signal line Lsig by the charge amplifier circuit that includes the charge amplifier 172 and the like. Then, A/D conversion is performed on each signal voltage (the output voltage Vca from the charge amplifier 172) so converted by the A/D converter 175 via each S/H circuit 173 and the multiplexer circuit 174, to generate the output data Dout (the image pickup signal) which is in the form of a digital signal. Respective pieces of output data $D_{out}$ are output in order from the respective column selecting sections 17 in the above-mentioned manner and transmitted to the outside (or input into a not-illustrated internal memory). In the following, an image pickup driving operation as mentioned above will be described in detail.

(Operations in Exposing Term and Reading Term)

Figure 7A:
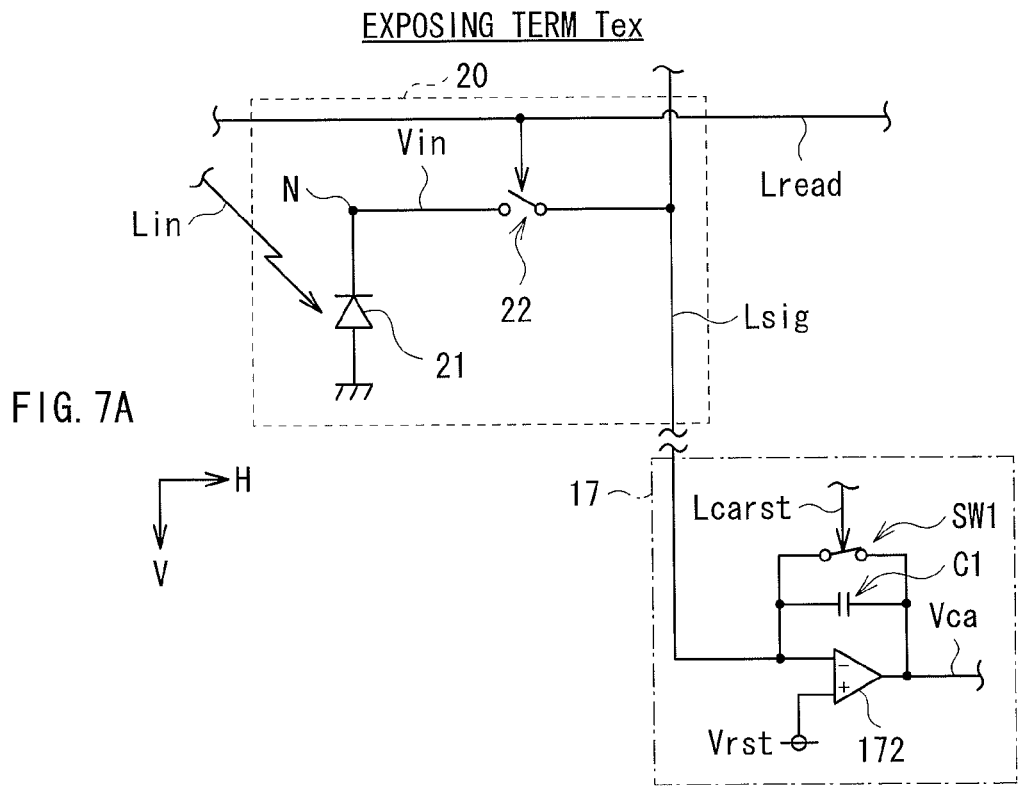
FIG. 7A is a circuit diagram illustrating one example of an operation state in an exposing term.
Figure 7B:
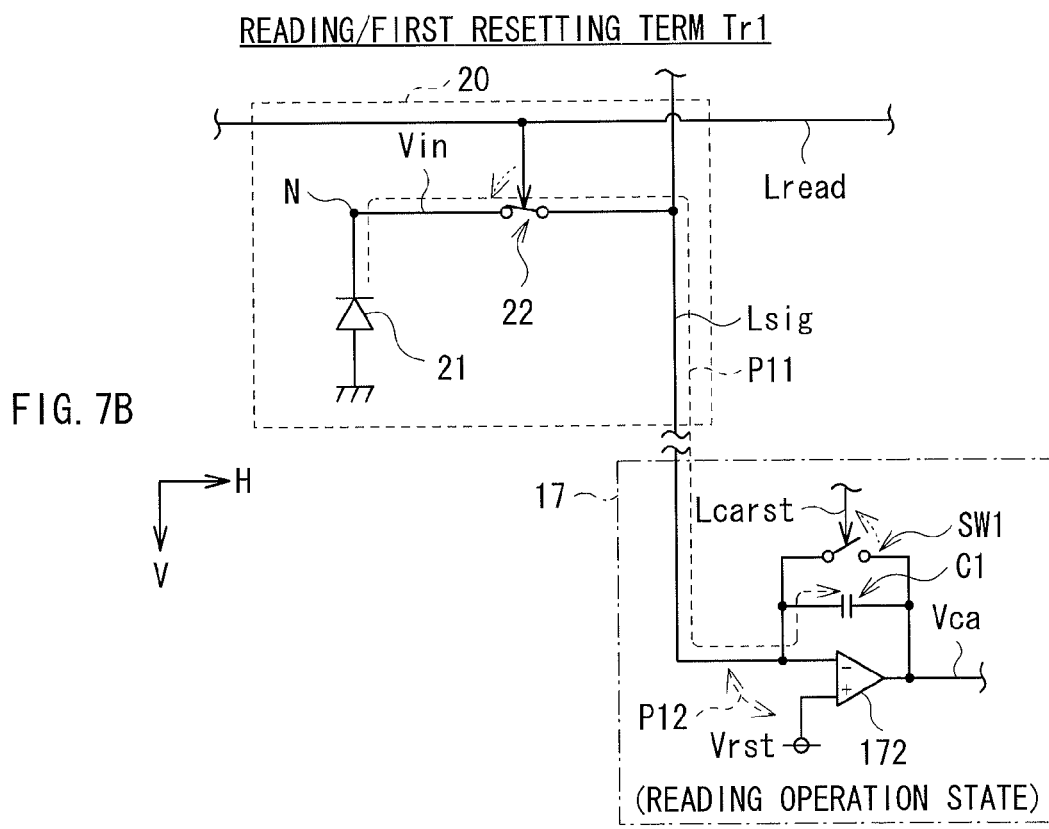
FIG. 7B is a circuit diagram illustrating one example of an operation state in a reading/first resetting term.
Figure 8:
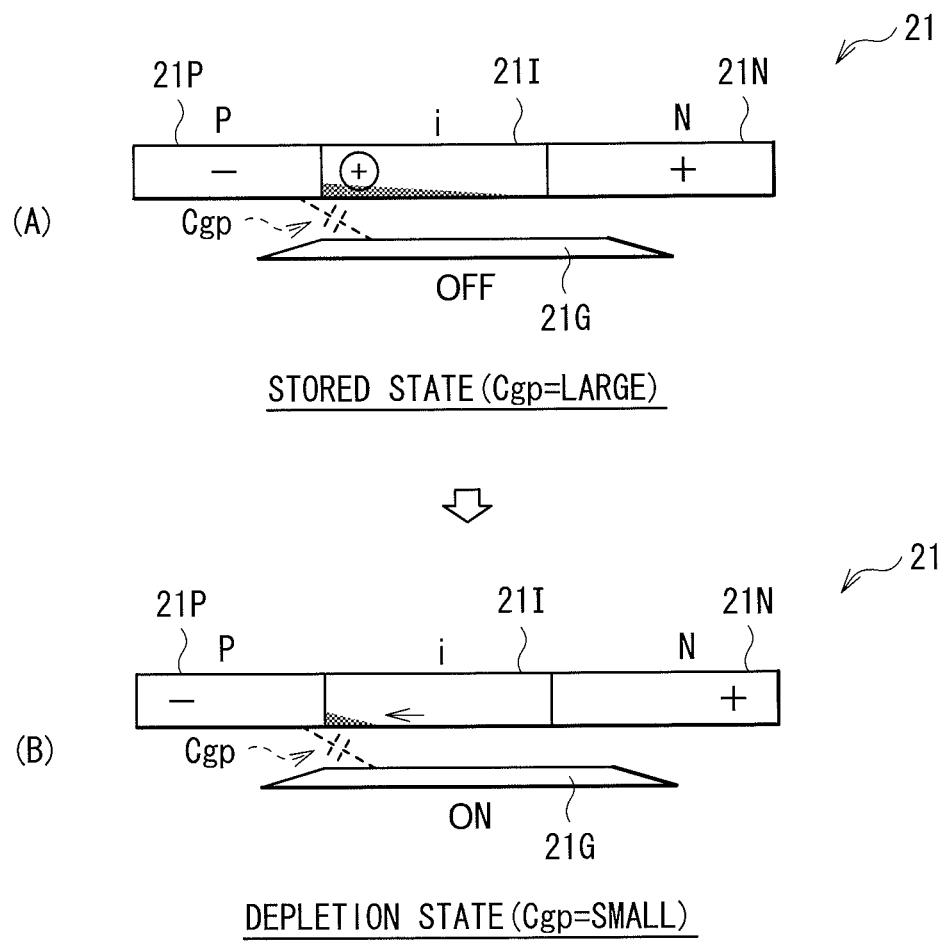
FIG. 8 is a schematic diagram illustrating a PIN type photodiode having a lateral structure, in which (A) illustrates an example of a stored state thereof and (B) illustrates an example of a depletion state thereof.

FIG. 7A and FIG. 7B illustrate operational examples of the pixel 20 and the charge amplifier circuit in the column selecting section 17 in an exposing term and a reading term. It is to be noted that, in the following, the on/off state of the transistor 22 will be illustrated using a switch for the convenience of explanation.

First, the transistor 22 is in the off-state in the exposing term Tex as illustrated in FIG. 7A. The signal charge which is based on the image pickup light Lin which has been incident upon the photoelectric conversion device 21 in the pixel 20 is stored in the storage node N, and is not output toward the signal line Lsig (is not read out) in this state. On the other hand, since the charge amplifier circuit is in a state that a later-described amplifier resetting operation (a resetting operation of the charge amplifier circuit) has been already performed, the switch SW1 is in the on-state and a voltage follower circuit is formed consequently.

Then, after the exposing term Tex has expired, an operation (a reading operation) of reading out the signal charge from the pixel 20 and an operation (a resetting operation, a pixel resetting operation, or the like) of resetting (emitting) the signal charge stored in the pixel 20 are performed. In the present embodiment, since the pixel 20 includes the passive type pixel circuit, the resetting operation is performed with execution of the above-mentioned reading operation. It is to be noted that this resetting operation corresponds to a firstly executed resetting operation (a first resetting operation) in a plurality of resetting operations which will be described later. Therefore, in the following, description will be made by referring this reading term to as a "reading/first resetting term Tr1" or simply to as the "term Tr1".

Specifically, in the reading/first resetting term Tr1, the transistor 22 enters the on-state, by which the signal charge is read out from the storage node N in the pixel 20 toward the signal line Lsig (see an arrow P11 in the drawing) as illustrated in FIG. 7B. The signal charge so read is input into the charge amplifier circuit. On the other hand, the switch SW1 is in the off-state (the charge amplifier circuit is in a reading operation state) in the charge amplifier circuit. Therefore, the signal charge input into the charge amplifier circuit is stored in the capacitative element C1, and the signal voltage (the output voltage Vca) corresponding to the stored charge is output from the charge amplifier 172. It is to be noted that the charge stored in the capacitative element C1 is reset (an amplifier resetting operation is performed) by bringing the switch SW1 into the on-state when the later-described amplifier resetting operation is executed.

A resetting operation (the first resetting operation) as described below is performed with execution of the reading operation as mentioned above in the reading/first resetting tem Tr1. That is, the first resetting operation is executed by utilizing a virtual short (imaginary short) phenomenon in the charge amplifier circuit (the charge amplifier 172) as designated by an arrow P12 in the drawing. Describing in detail, since the voltage on the negative input terminal side (the signal line Lsig side) of the charge amplifier 172 becomes almost equal to the reset voltage Vrst which is applied to the positive input terminal thereof under the influence of the virtual short phenomenon, the storage node N is also reset to the reset voltage Vrst. In the present embodiment using the passive type pixel circuit, the storage node N is reset to the predetermined reset voltage Vrst with execution of the above-mentioned reading operation in the reading/first resetting term Tr1 as described above.

(Residue of Signal Charges after Reading/First Resetting Term)

Although the resetting operation is executed with execution of the reading operation in the reading/first resetting term Tr1 as described above, it may sometimes occur that some of the ever stored signal charges remain (stay behind) in the pixel 20 even after the term Tr1. When some of the signal charges remain in the pixel 20, an afterimage may be generated under the influence of the residual charges in execution of the next reading operation (when an image is picked up in the next frame term) and the quality of the picked-up image may be deteriorated. In the following, residue of signal charges as mentioned above will be described in detail with reference to FIG. 8 to FIG. 12.

Figure 9:
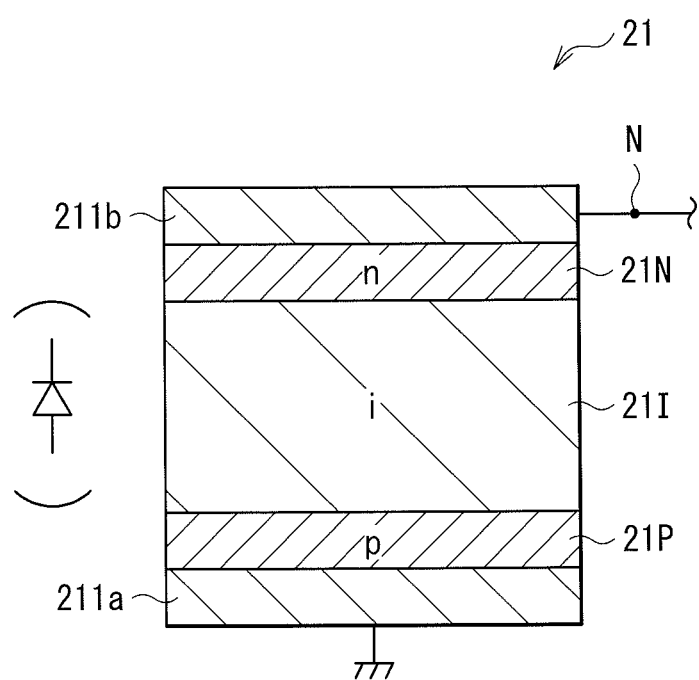
FIG. 9 is a schematic sectional diagram illustrating one example of a PIN type photodiode having a vertical structure.

Here, when the photoelectric conversion device 21 is a PIN type photodiode (a thin-film photodiode), it is broadly divided into the ones having the following two structures specifically. That is, it is divided into the one having a so-called lateral (horizontal) structure as illustrated in (A) and (B) of FIG. 8 and the one having a so-called vertical (longitudinal) structure as illustrated in FIG. 9.

In the lateral structure one, the photoelectric conversion device 21 includes a p-type semiconductor layer 21P, an intrinsic semiconductor layer (i layer) 21I, and an n-type semiconductor layer 21N in this order in a lateral direction (an in-lamination plane direction). It also includes a gate electrode 21G which is oppositely disposed in the vicinity of the intrinsic semiconductor layer 21I via a gate insulating film (not illustrated). On the other hand, in the vertical structure one, the photoelectric conversion device 21 includes, for example, a lower electrode 211a, the p-type semiconductor layer 21P, the intrinsic semiconductor layer 21I, the n-type semiconductor layer 21N, and an upper electrode 211b in this order in a vertical direction (a laminated layer direction). It is to be noted that in the following, description will be made assuming that the photoelectric conversion device 21 is the PIN type photodiode having the lateral structure in the above-mentioned two structures.

(Mechanism of Signal Charge Residue)

As one of the reasons for occurrence of signal charge residue as described above, it is thought that the charges in the pixels 20 are saturated under the influence of natural light (in particular, strong natural light). In the photoelectric conversion device 21, the intrinsic semiconductor layer 21I is brought into one of a stored state (a saturated state), a depletion state, and an inversion state with a gate voltage which is applied to the gate electrode 21G. However, in the thin-film photodiode, a time which is on the order of several hundred µs may be desired for a transition from a state ((A) of FIG. 8) that the charges are induced at an interface on the side of the gate electrode 21G to the depletion state ((B) of FIG. 8) when it is in the stored state or the inversion state. In general, since the photosensitivity of the PIN type photodiode is maximized in the depletion state, it is used in the depletion state. However, for example, when it is irradiated with the strong natural light and enters a state of Vnp<0V, it undergoes a transition to the stored state. It is to be noted that Vnp is the potential of the n-type semiconductor layer 21N when viewed from the side of the p-type semiconductor layer 21P.

Therefore, for example, even when the environment changes to a dark state immediately after irradiated with the strong natural light and a resetting operation (the first resetting operation) is executed to bring it back to the state of Vnp>0V, the transition from the stored state to the depletion state may not occur for several hundred µs. Here, it is known that capacitance characteristics of the PIN type photodiode differ depending on whether it is in the depletion state or in the stored or inversion state under the influence of the charges induced at the interface on the side of the gate electrode 21G described above. Specifically, a parasitic capacitance Cgp which is formed between the gate electrode 21G and the p-type semiconductor layer 21P is increased in the stored state and is decreased in the depletion state as illustrated in (A) and (B) of FIG. 8.

Here, in the PIN-type photodiode (the photoelectric conversion device 21) which is connected to the storage node N, when the parasitic capacitance Cgp is varied depending on whether it is in the depletion state or in the stored or inversion state, the total coupling amount (the size of the parasitic capacitance) in the pixel 20 changes with a state transition as mentioned above. Therefore, information (the charge) on light which has been incident just before the term Tr1 may remain in the storage node N even after the reading/first resetting term Tr1. When the charges in the pixel 20 are saturated by being irradiated with the strong natural light with a mechanism as mentioned above, some of the signal charges which have been ever stored just before the reading/first resetting term Tr1 involving the resetting operation remain in the pixel 20 even after the term Tr1.

On the other hand, in some cases, the signal charges may remain for reasons as described below, not limiting the above-mentioned case (i.e., the charges are saturated under the influence of the strong natural light). That is, residual charges may generate also in association with generation of a transient-decay current from the photoelectric conversion device 21 (the PIN type photodiode).

(A) and (B) of FIG. 10 illustrate examples of an energy band structure (a relation between the position and the energy level of each layer) in the above-mentioned PIN type photodiode. Many defect levels Ed are present on the intrinsic semiconductor layer 21I as apparent from these drawings. A state that a charge "e" is captured (trapped) in each of these defect levels Ed is observed just after the reading/first resetting term Tr1 as illustrated in (A) of FIG. 10. However, when a certain time passes from the reading/first resetting term Tr1, the charge "e" trapped in the defect level Ed is emitted from the intrinsic semiconductor layer 21I to the outside of the photodiode (the photoelectric conversion device 21) (see a broken line with an arrow), for example, as illustrated in (B) of FIG. 10. Thus, the above-mentioned transient-decay current (a current Idecay) is generated from the photoelectric conversion device 21.

Figure 11A:
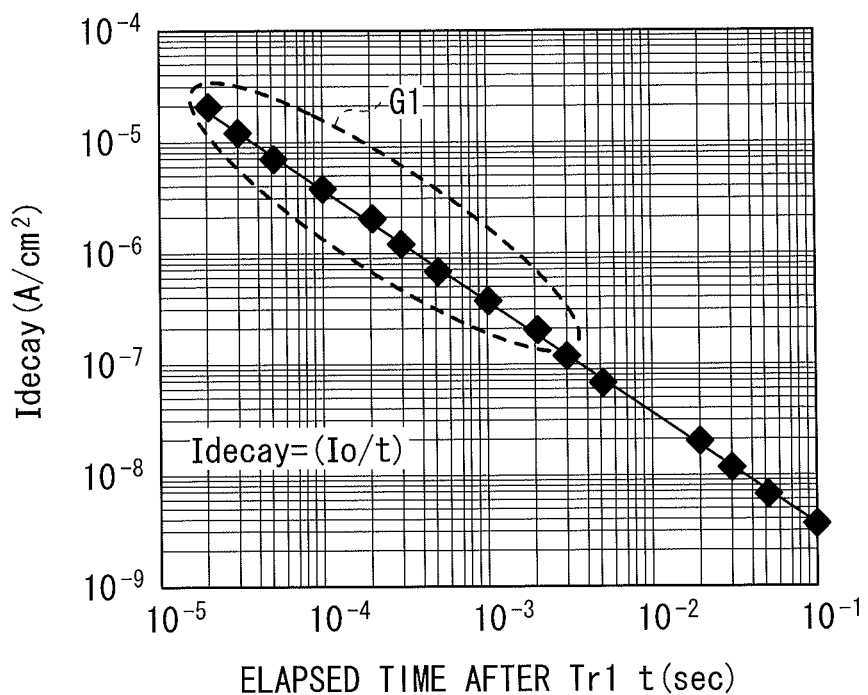
FIG. 11A and FIG. 11B are characteristic diagrams illustrating examples of a relation between an elapsed time and a transient-decay current after the reading/first resetting term.
Figure 11B:
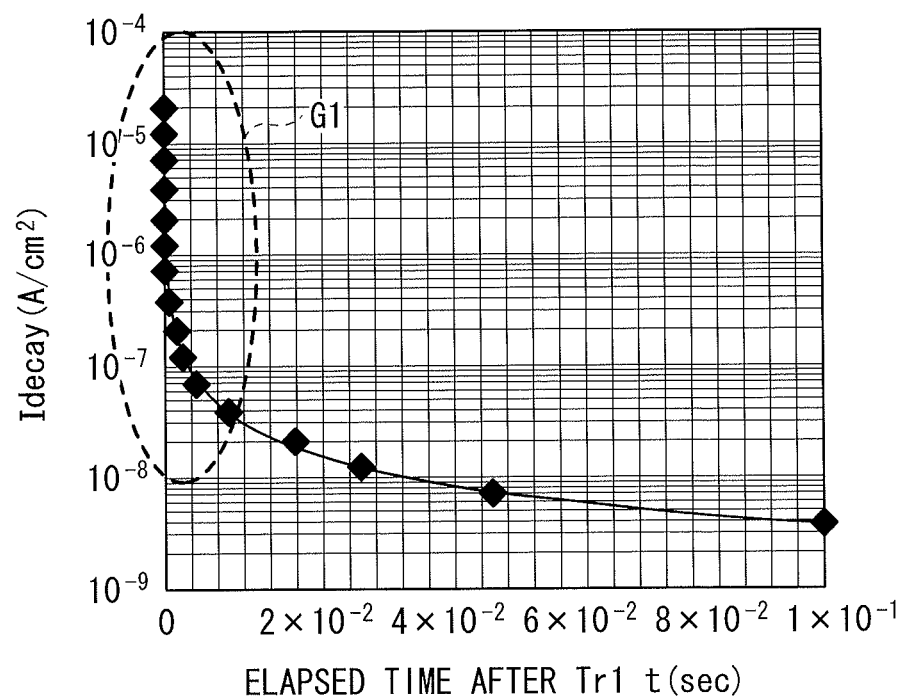
Figure 12:
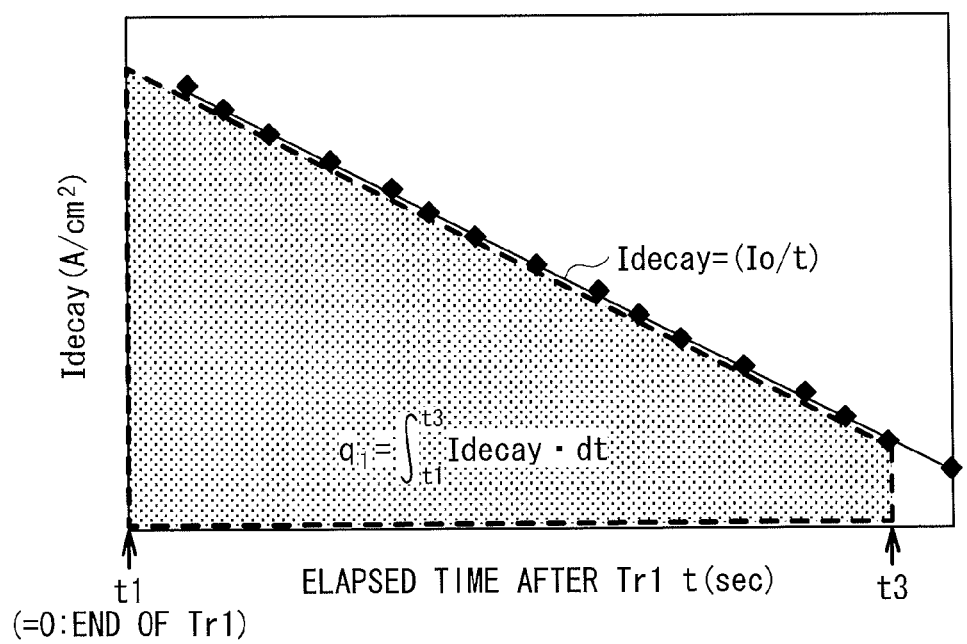
FIG. 12 is a characteristic diagram illustrating an example of a relation between a residual charge amount and the transient-decay current.

Here, examples of a relation between an elapsed time "t" after the reading/first resetting term Tr1 and the current Idecay are illustrated in FIG. 11A and FIG. 11B. Both the vertical axis and horizontal axis are plotted on a logarithmic (log) scale in FIG. 11A and the vertical axis is plotted on a logarithmic scale and the horizontal axis is plotted on a linear scale in FIG. 11B. Parts (G1) surrounded by broken lines are mutually corresponding parts in the drawings. As apparent from these drawings, the current Idecay has a tendency to be synergistically reduced with time at the end (t=0) of the reading/first resetting term Tr1 (Idecay=Io/t, Io: a constant value). In addition, it is apparent that a residual charge (designated by q1) that generates at that time is obtained by integrating the current Idecay=(Io/t) with the elapsed time "t", for example, as illustrated in FIG. 12. The residual charge generates in the pixel 20 also with the transient-decay current that generates from the photoelectric conversion device 21 mentioned above.

The residual charge q1 generates in the pixel 20 even after the reading/first resetting term Tr1 involving the resetting operation for reasons (charge saturation caused by irradiation with the strong natural light and generation of the transient-decay current) as described above.

(Plurality of Resetting Operations)

Figure 13:
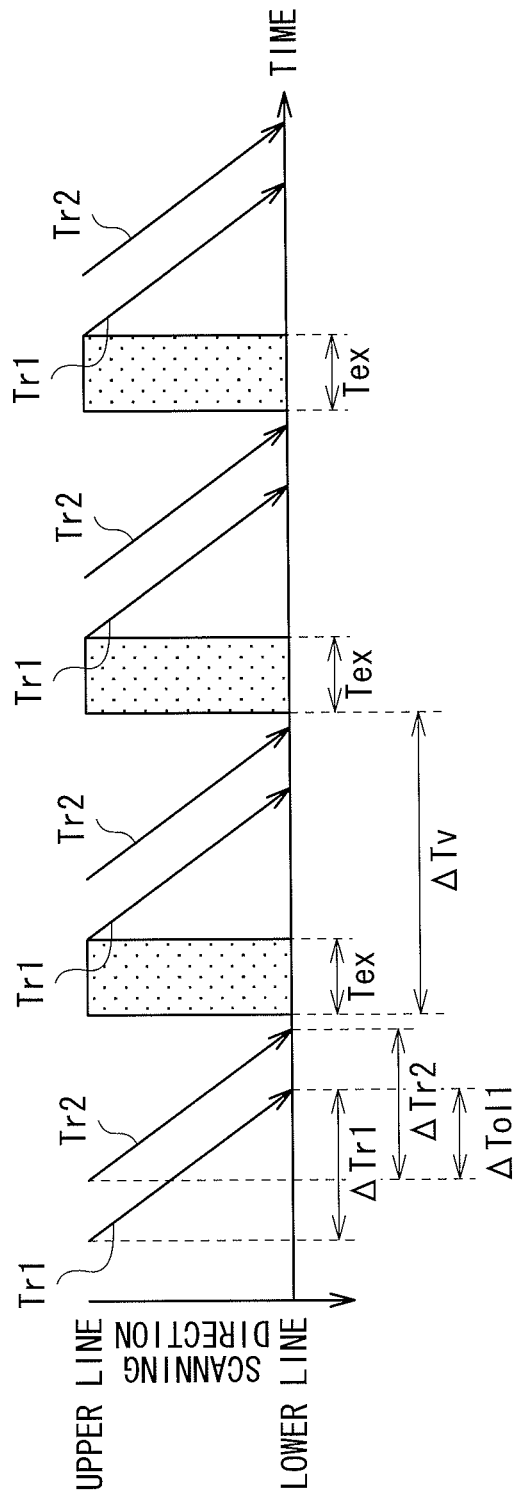
FIG. 13 is a timing chart illustrating an example of the outline of a line-sequential image picking-up operation according to an embodiment.

In this embodiment, the plurality of resetting operations (here, two operations in all, that is, the resetting operation performed in the reading/first resetting term Tr1 is included) are performed. In addition, read driving and reset driving are performed line-sequentially as described later. Describing in detail, read driving and plural-time reset driving are performed by single line-sequential driving so as to reduce the residual charges and to suppress the afterimage which would generate by the residual charges. Specifically, a second-time resetting operation (a second resetting operation) is performed in a second resetting term Tr2 with a predetermined time interval left after the exposing term Tex has elapsed and then the reading operation and the first resetting operation have been performed in the term Tr1 in a one-vertical term (a one-frame term) ΔTv as illustrated in FIG. 13. Each of the reading operation and resetting operations in the terms Tr1 and Tr2 is line-sequentially performed (line-sequential read driving and line-sequential reset driving are performed in each pixel 20 under the control of the system control section 16) in the above-mentioned operations.

(Examples of Line Sequential Driving)

Figure 14:
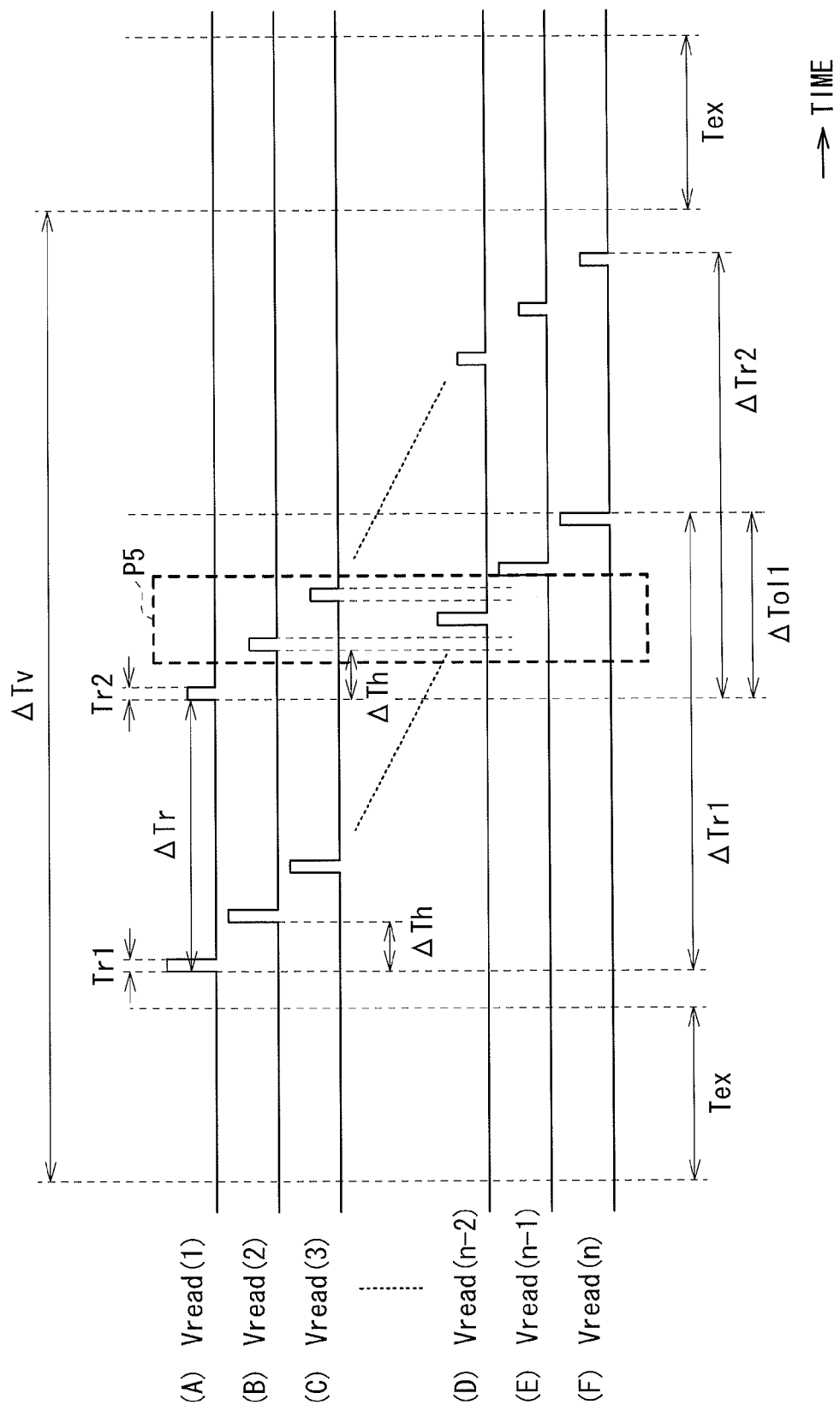
FIG. 14 is a timing waveform diagram illustrating details of the line-sequential image picking-up operation.
Figure 15:
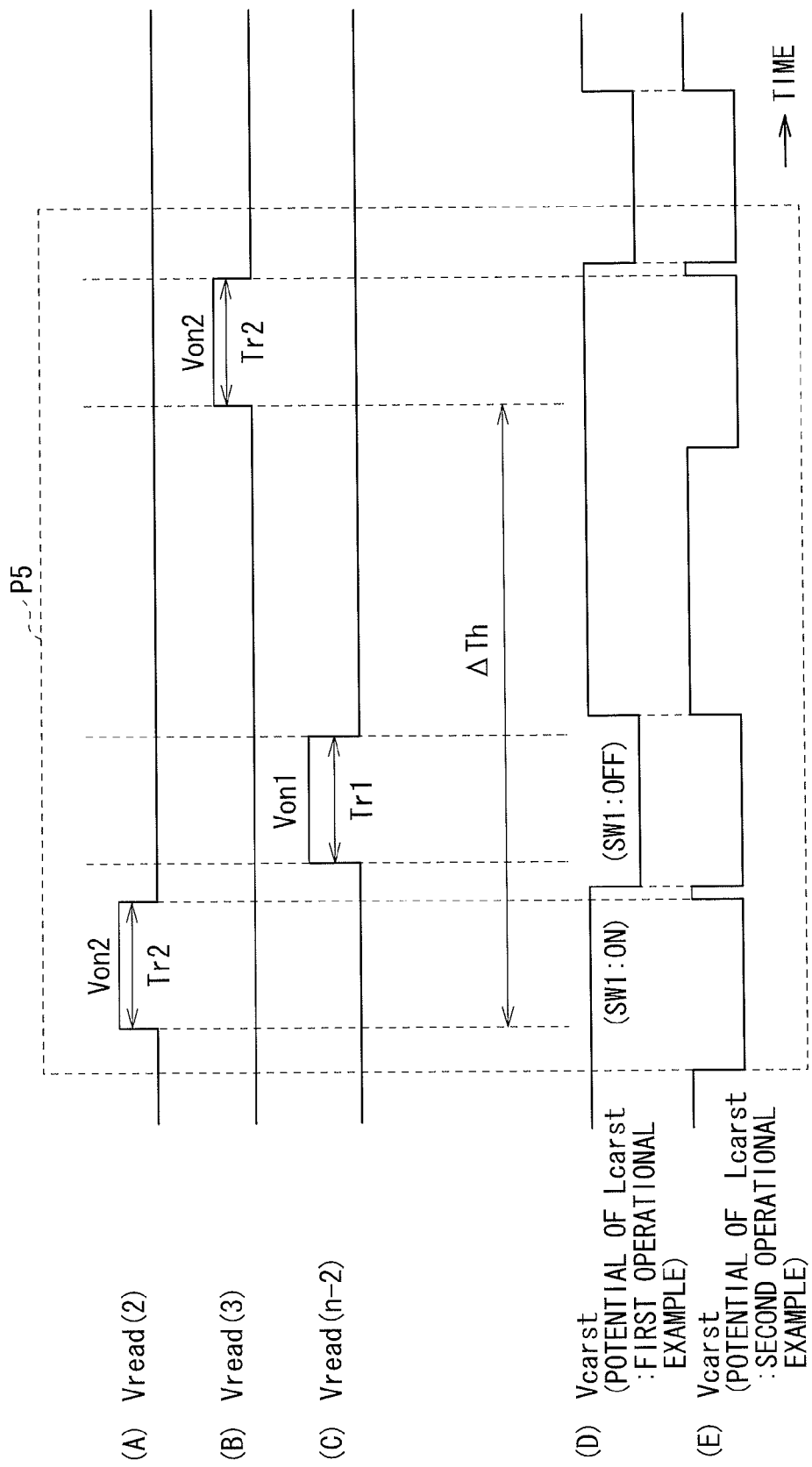
FIG. 15 is a partially enlarged diagram of the timing waveforms illustrated in FIG. 14.
Figure 16:
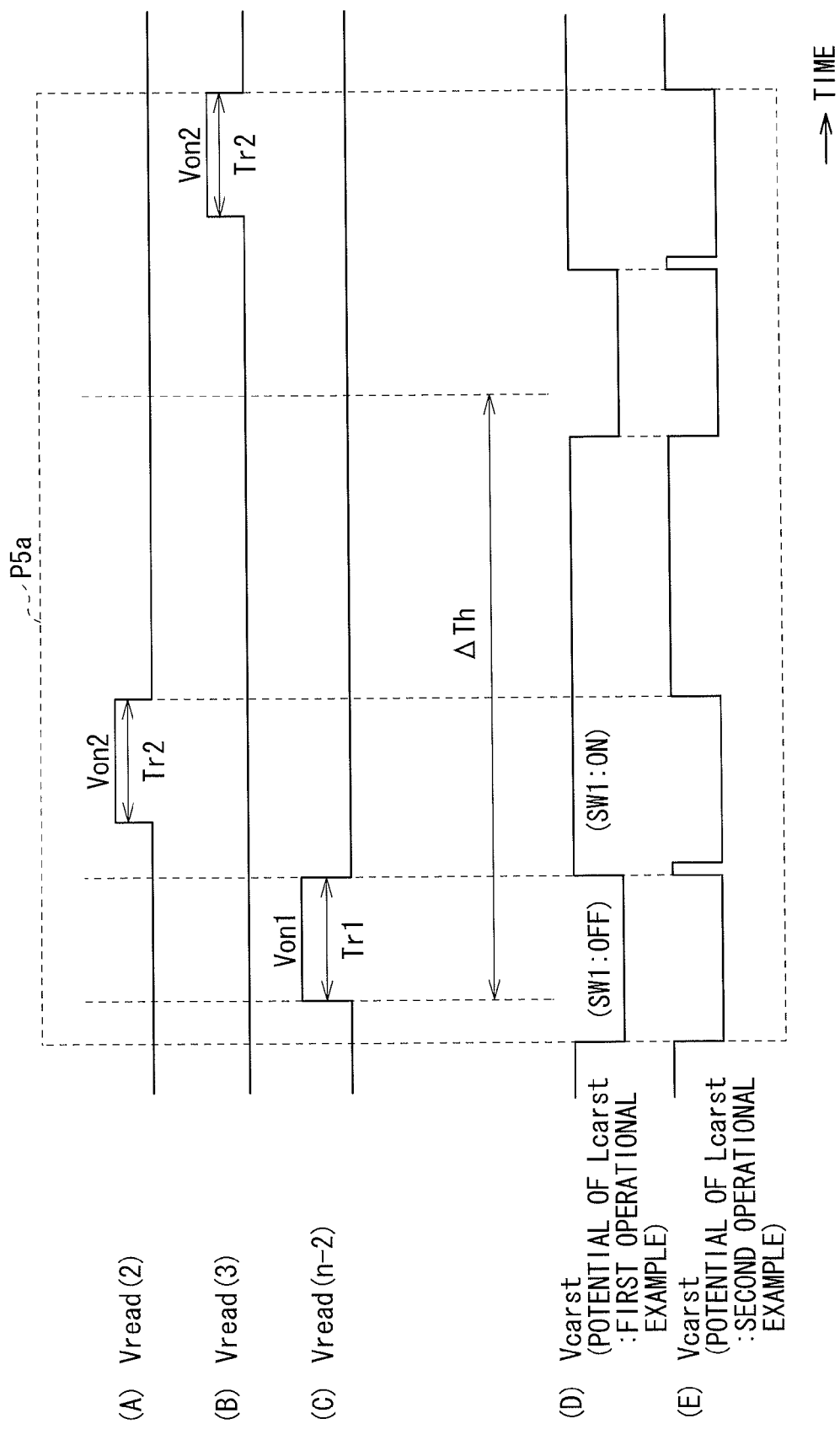
FIG. 16 is a timing waveform diagram illustrating another operational example of the line-sequential image picking-up operation according to an embodiment.
Figure 17:
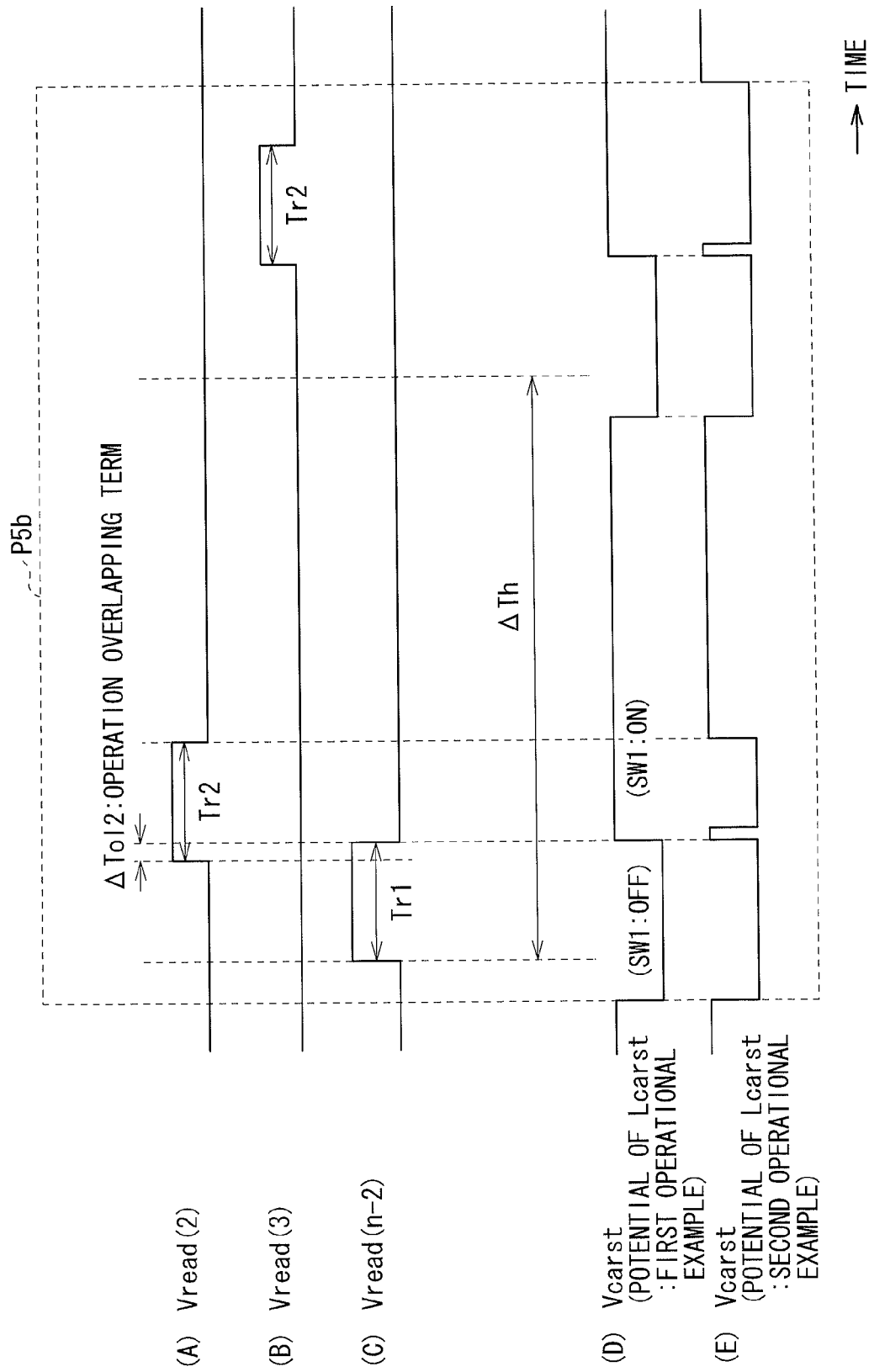
FIG. 17 is a timing waveform diagram illustrating a further operational example of the line-sequential image picking-up operation according to an embodiment.

Examples of timings of operations in line sequential image pickup driving (the line sequential read driving and the line sequential reset driving) are illustrated in FIG. 14 to FIG. 17. FIG. 14 illustrates an example of the line sequential image pickup driving according to the present embodiment in the form of a timing waveform diagram. Here, (A) to (F) of FIG. 14 illustrate examples of timing waveforms of potentials Vread (1) to Vread (3), and Vread (n-2) to Vread (n) of the read control lines Lread (1) to Lread (3), and Lread (n-2) to Lread (n). In addition, ΔTh in the drawings denotes one horizontal term (one horizontal scanning term). In FIG. 15 to FIG. 17, examples of a potential Vcarst of the above-mentioned amplifier reset control line Lcarst are illustrated with respect to the above-mentioned first operational example ((D) of each drawing) and the second operational example ((E) of each drawing).

A partially superimposing term (a driving overlapping term ΔTol1) is present in a term (a line sequential driving term ΔTr1) during which the first resetting operations or the like (the operations executed in the reading/first resetting term Tr1) for all lines are executed and a term (a line sequential driving term ΔTr2) during which the second resetting operations for all lines are executed, for example, as illustrated in (A) to (F) of FIG. 14.

In the driving overlapping term ΔTol1, the terms (the terms Tr1 and Tr2) of respective resetting operations are set as follows. Specifically, each resetting term (each term Tr1 in the line sequential driving term ΔTr1) for the first line sequential reset driving and each resetting term (each term Tr2 in the line sequential driving term ΔTr2) for the second line sequential reset driving are set as follows. That is, in the driving overlapping term ΔTol1, the terms are set such that a non-superimposing term (a non-overlapping term) in which each reading/first resetting term Tr1 and each resetting term Tr2 do not overlap each other is at least partially present in the drive overlapping term ΔTol1 (see, for example, a term designated by P5 in FIG. 14). (A) to (E) of FIG. 15 illustrate examples of enlarged waveforms in the vicinity of the term designated by P5.

Each reset driving is executed without overlapping the reading/first resetting term Tr1 and the second resetting term Tr2 each other in the drive overlapping term ΔTol1 as illustrated in (A) to (E) of FIG. 15. In this example, the potential Vread (the on-state potential Von1 or the on-state potential Von2) corresponding to the row scan signal is applied in order of Vread (2) (the second resetting term Tr2), Vread (n-2) (the reading/first resetting term Tr1), and Vread (3) (the second resetting term Tr2) in the term designated by P5. On the other hand, in another term designated by P5a, for example, illustrated in (A) to (E) of FIG. 16, the potential Vread is applied in order of Vread (n−2) (the reading/first resetting term Tr1), Vread (2) (the second resetting term Tr2), and Vread (3) (the second resetting term Tr2). In addition, in a further term designated by P5b, for example, illustrated in (A) to (E) of FIG. 17, the above-mentioned non-overlapping term is set only in a partial term in each reading/first resetting term Tr1 and each second resetting term Tr2 in the drive overlapping term ΔTol1. In other words, a superimposing term (an operation overlapping term ΔTol2) is only partially present in the reading/first resetting term Tr1 and the second resetting term Tr2. In the both examples, the non-overlapping term is set at least partially in the overlapping term ΔTol1.

The timings and the like of respective operations in line sequential image pickup driving as mentioned above may be implemented by the row scan circuit 13 that includes the unit circuit 130, for example, illustrated in FIG. 4. Specifically, they are implemented by the plurality of columns of shift register circuits 131 and 132 which are disposed corresponding to the number of times of executing the line sequential reset driving, and by the logic circuits (the AND circuits 133A to 133D and the OR circuits 134A and the 134B) that generate a logical sum signal of the signals output from the each column of the shift register circuits 131 and 132 while controlling the validity term of each output signal.

The above-mentioned non-overlapping term is set to be at least partially present in the resetting terms (the reading/first resetting term Tr1 and the second resetting term Tr2) in the drive overlapping term ΔTol1 between the line sequential driving term ΔTr1 and the line sequential driving term ΔTr2 as described above. Thus, it is allowed to optionally set the term, the timing, and the like of each resetting operation when the line sequential reset driving is executed the plurality of times. In particular, when the non-overlapping term between the reading/first resetting term Tr1 and the second resetting term Tr2 in the drive overlapping term ΔTol1 is set only partially as illustrated in FIG. 17, it is allowed to implement acceleration (an increase in frame rate) of the line sequential image pickup driving as compared with other examples (FIG. 15 and FIG. 16).

It is to be noted that it is difficult for an existing standard-type row scan circuit (a gate driver circuit) to perform operations of pixels which are connected to different scan lines at timings or the like at least parts of which do not overlap each other, as compared with the row scan circuit 13 according to the present embodiment that implements the operation timings and the like as mentioned above.

In the following, an image pickup driving operation for one line executed in line sequential image pickup driving as mentioned above will be described in detail.

Figure 18:
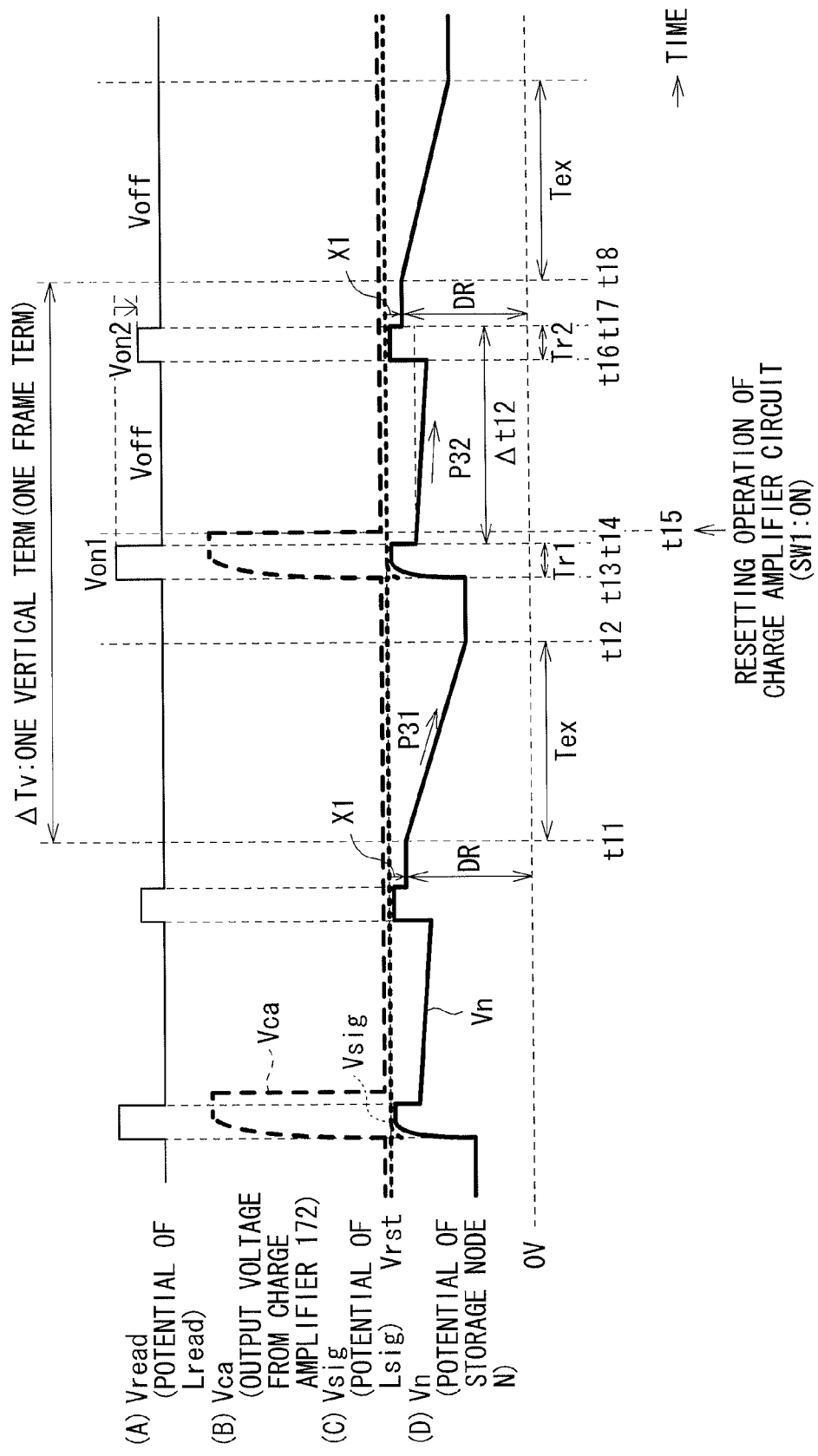
FIG. 18 is a timing waveform diagram illustrating an example of a one-line image picking-up operation.

(A) of FIG. 18 illustrates an example of a timing waveform of the potential Vread of the read control line Lread, (B) of FIG. 18 illustrates an example of a timing waveform of the output voltage Vca from the charge amplifier 172, (C) of FIG. 18 illustrates an example of a timing waveform of the potential Vsig of the signal line Lsig, and (D) of FIG. 18 illustrates an example of a timing waveform of the potential Vn of the storage node N. It is to be noted that the respective timing waveforms are waveforms observed in the one-frame term ΔTv and its preceding and succeeding terms.

In the one-frame term ΔTv, the exposing operation is performed as described above (FIG. 7A) first in the exposing term Tex (between timings t11 and t12), and the incident image pickup light Lin is converted (photoelectric-converted) into the signal charge by the photoelectric conversion device 21 in each pixel 20. Then, the potential Vn of the storage node N gradually changes (P31 in (D) of FIG. 18) as the signal charges are stored in the storage node N in each pixel 20. Here, since the cathode side of the photoelectric conversion device 21 is connected to the storage node N, the potential Vn gradually drops from the reset voltage Vrst side toward 0V in the exposing term Tex.

Next, in the reading/first resetting term Tr1 (between timings t13 and t14), the first resetting operation is executed together with the reading operation as described above. In the above-mentioned case, the on-state potential Von1 is applied to the read control line Lread in the present embodiment. Specifically, the potential Vread is switched from the off-state potential Voff to the on-state potential Von1 at the timing t13, and is switched from the on-state potential Von1 to the off-state potential Voff at the timing t14. It is to be noted that the on-state potential Von1 is a potential (a high-side potential (for example, a positive potential) in a voltage pulse) at which the transistor 22 may be switched from the off-state to the on-state. The off-state potential Voff is a potential (a low-side potential (for example, a negative potential) in the voltage pulse) at which the transistor 22 may be switched from the on-state to the off-state. In addition, at the next timing t15, the switch SW1 of the charge amplifier circuit enters the on-state, by which the charge stored in the capacitative element C1 in the charge amplifier circuit is reset (the amplifier resetting operation is executed).

The residual charge q1 generates after the reading/first resetting term Tr1 for reasons as mentioned above and the potential Vn of the storage node N gradually drops (P32 in (D) of FIG. 18). Therefore, the second resetting operation which will be described hereinbelow is executed in the second resetting term Tr2 (between timings t16 and t17) that comes after the reading/first resetting Tr1 with a predetermined time interval left between them.

(Second Resetting Operation)

Figure 19A:
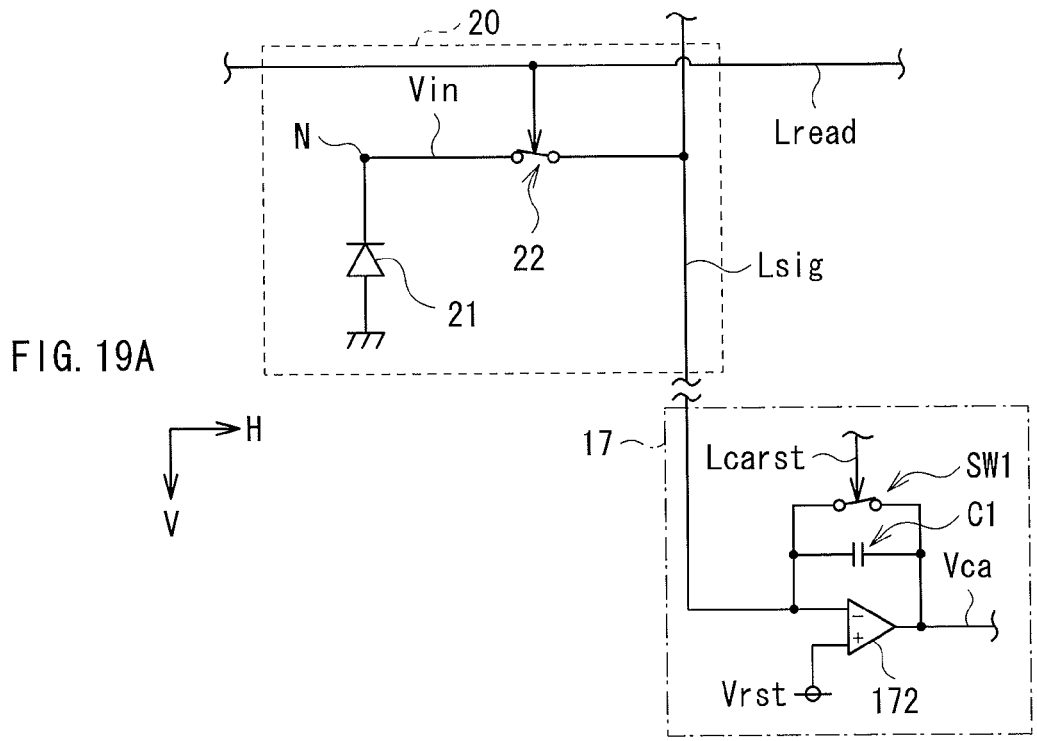
FIG. 19A and FIG. 19B are circuit diagrams illustrating examples of an operation state in a second resetting term.

Specifically, the second resetting operation may be performed in a manner exemplified by, for example, a first operational example illustrated in FIG. 19A in the second resetting term Tr2. That is, the transistor 22 in the pixel 20 enters the on-state and the switch SW1 of the charge amplifier circuit also enters the on-state. Thus, a voltage follower circuit using the charge amplifier 172 is formed. Therefore, a voltage on the negative input terminal side (on the signal line Lsig side) becomes almost equal to the reset voltage Vrst which is applied to the positive input terminal in the charge amplifier 172 with the aid of its feedback characteristics. In the first operation example, the potential Vn of the storage node N in the pixel 20 is displaced to the reset voltage Vrst (the second resetting operation is executed) by utilizing the feedback characteristics of the charge amplifier 172 as described above.

Figure 19B:
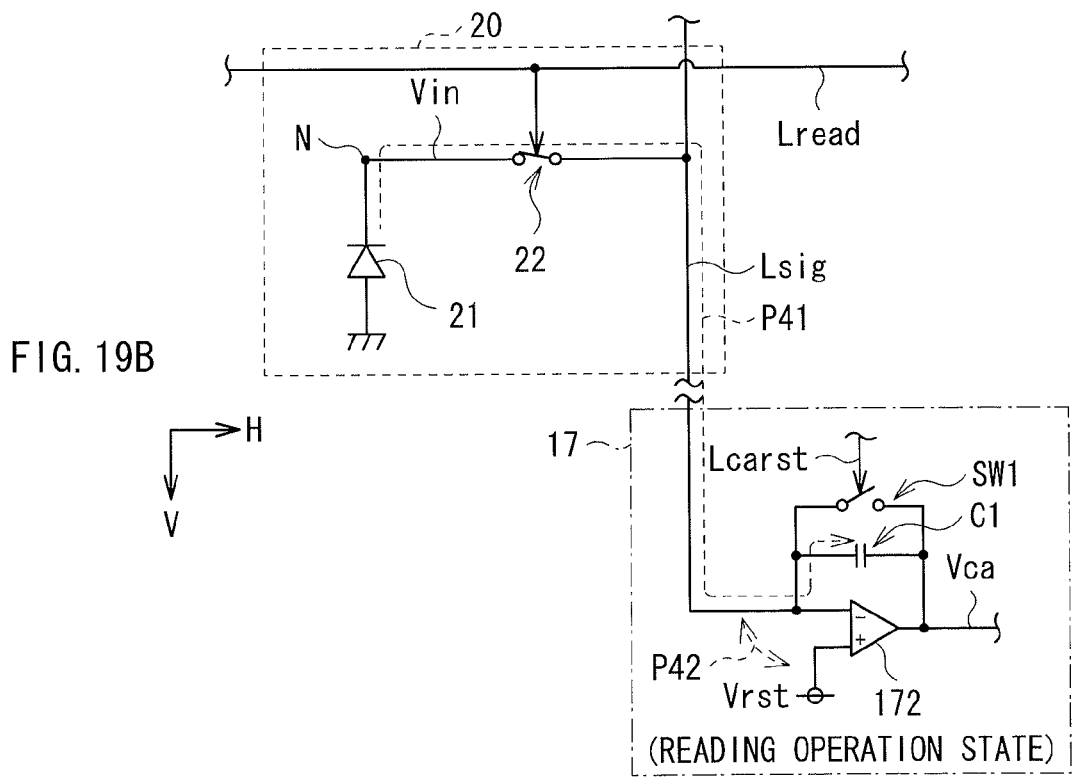

Alternatively, the second resetting operation may be executed in a manner exemplified by a second operational example illustrated in FIG. 19B. That is, the second resetting operation may be executed by utilizing the virtual short phenomenon of the charge amplifier circuit as in the case of the above-mentioned first resetting operation (P42 in FIG. 19B). The potential Vn of the storage node N in the pixel 20 is displaced to the reset voltage Vrst also with the aid of the virtual short phenomenon. However, in the example, since the transistor 22 in the pixel 20 is in the on-state and the switch SW1 of the charge amplifier circuit is in the off-state similarly to the states in the reading/first resetting term Tr1, the charge amplifier circuit is in the reading operation state. That is, it is also allowed to read the charge remained in the storage node N by the charge amplifier circuit as indicted by an arrow P41 in FIG. 19B in the second operational example.

The operation of resetting the charge stored in the pixel 20 is intermittently and repetitively executed (the resetting operation is executed the plurality of times) in the one-frame term in the above-mentioned manner in the present embodiment. Specifically, here, the first resetting operation (in the reading/first resetting term Tr1) and the second resetting operation (in the second resetting term Tr2) are executed with the predetermined time interval left between them. Thus, the amount of residual charges q1 (the residues of the signal charges) in the pixel 20 after execution of the first resetting operation is reduced.

Figure 20:
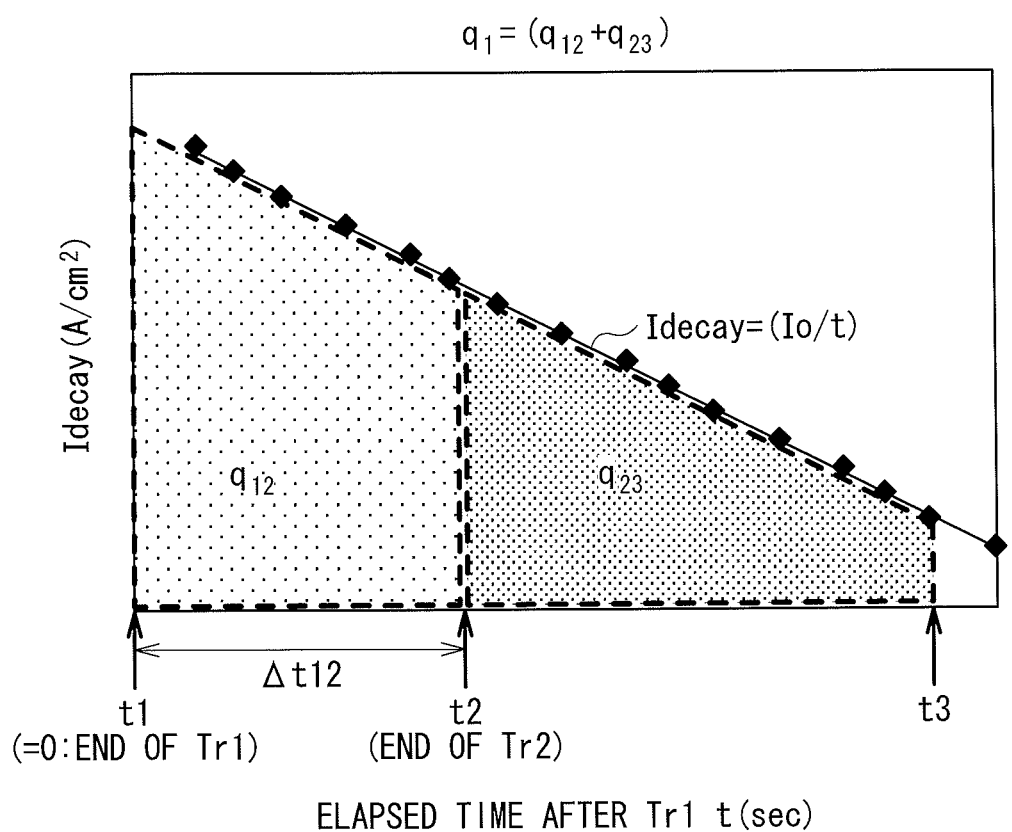
FIG. 20 is a characteristic diagram illustrating an example of a residual charge amount which is reduced by performing a second resetting operation.

Specifically, assuming that a time counted from the end (the end of the term Tr1) of the first resetting operation to the end (the end of the term Tr2) of the second resetting operation is $\Delta t12$, the reduced amount of charges in the residual charges q1 will be as illustrated, for example, in FIG. 20. That is, in the residual charges q1 described, for example, in FIG. 12, charges q12 of the amount corresponding to a time integrated value from the start t1 (=0) of the time $\Delta t12$ to the end t2 thereof are emitted (reduced) by executing the second resetting operation. It is to be noted that since an amount of charges q23 which is calculated by an expression (q1−q12)=q23 corresponds to the amount of charges remained after execution of the second resetting operation, it is desirable that the time $\Delta t12$ be set to be as long as possible.

Since the amount of residual charges q1 after execution of the first resetting operation is reduced by executing the plurality of resetting operations in the above-mentioned manner, it is allowed to suppress generation of the afterimage induced by the residual charges in execution of the next reading operation (when an image is picked up in the next frame term).

(Reduction of Charge Injection)

Figure 21:
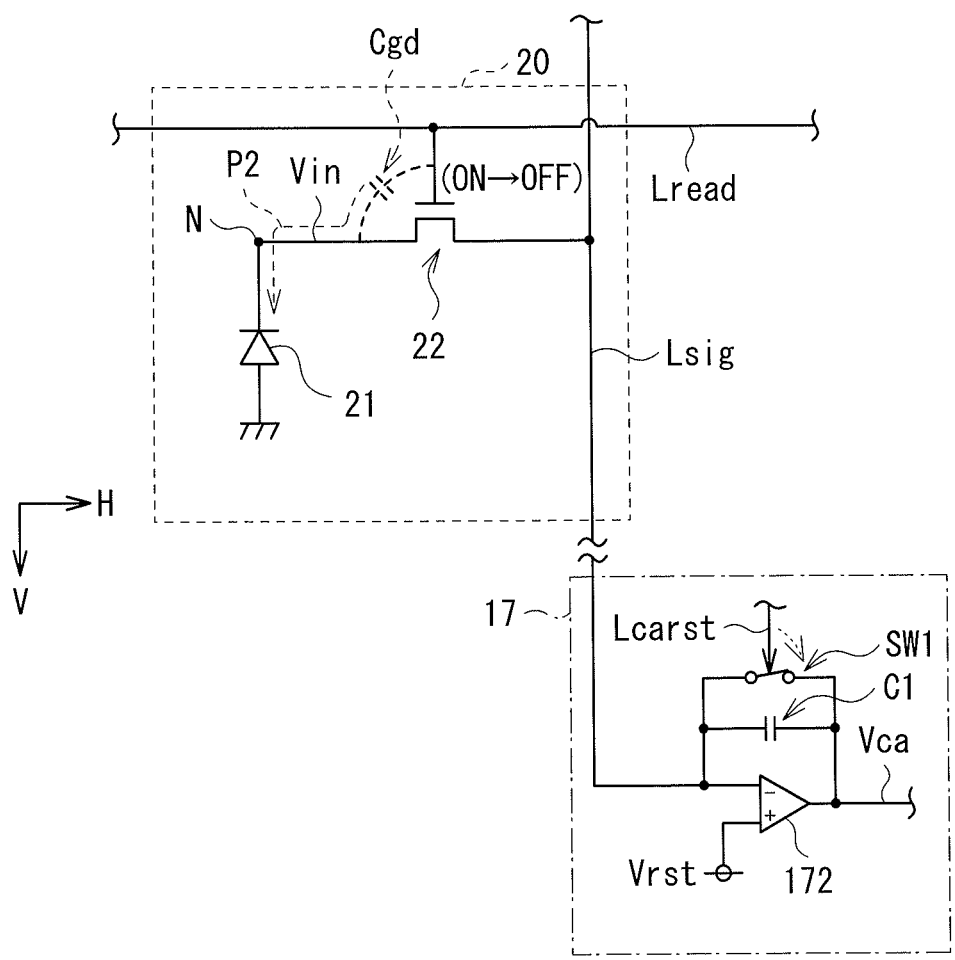
FIG. 21 is a circuit diagram illustrating an example of a charge distributing phenomenon (charge injection).

Although it is allowed to reduce the amount of residual charges to suppress generation of the afterimage by executing the plurality of resetting operation as mentioned above, a new phenomenon which is so-called charge injection occurs in association with reset driving executed for emission of the residual charges. That is, although the storage node N in the pixel 20 is reset to the predetermined reset voltage Vrst after the reading/first resetting term Tr1 as mentioned above, the transistor 22 shifts from the on-state to the off-state thereafter. In the above-mentioned case, for example, as illustrated in FIG. 21, the potential of the storage node N slightly changes from the reset voltage Vrst (see P2 in FIG. 21) caused by the charges stored in parasitic capacitances (a gate capacitance Cgc (not illustrated) formed between a gate and a channel of the transistor 22, and a parasitic capacitance Cgd formed between the gate and a drain thereof). Here, since the storage node N is connected to the cathode side of the photoelectric conversion device 21, the potential Vn drops from the reset potential Vrst by the amount corresponding to a predetermined potential (an arrow X1 in (D) of FIG. 18). Since occurrence of charge injection as mentioned above may cause noise in image pickup data Dout to induce deterioration of the image quality, it is desirable to reduce it as much as possible.

Figure 22:
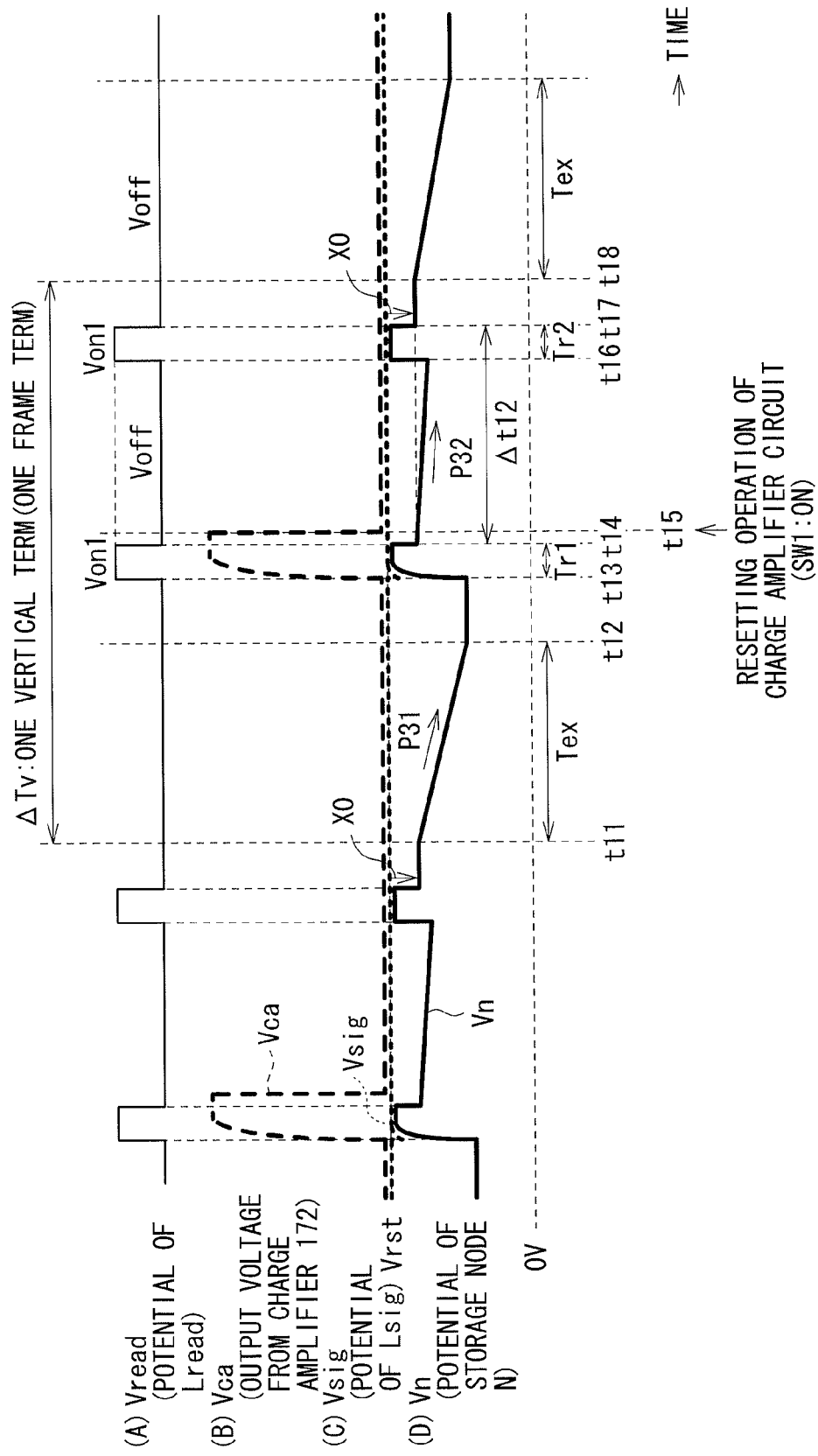
FIG. 22 is a timing waveform diagram illustrating an example of an image picking-up operation according to a comparative example.

COMPARATIVE EXAMPLE (A) to (D) of FIG. 22 illustrate examples of timing waveforms of an image pickup driving operation according to a comparative example of the present embodiment. In the comparative example, the image pickup driving operation is executed using a circuit configuration which is similar to that used in the present embodiment. In addition, it is configured to apply a two-valued (the on-state potential Von1 and the off-state potential Voff) voltage pulse to the read control line Lread. In the comparative example, the on-state potential Von1 is applied as the potential Vread both in the first and second resetting operations. Specifically, the same on-state potential Von1 is applied in respective terms between timings t13 and t14 and between timings t16 and t17.

Charge injection as mentioned above occurs with execution of the resetting operation also in the comparative example. However, when the on-state potential Von1 which is the same as for the first resetting operation is applied in execution of the second resetting operation, charge injection is more likely to occur. Thus, a potential drop (an arrow X0 in (D) of FIG. 22) from the reset potential Vrst is increased. In addition, the potential drop narrows a dynamic range DR0 for charge storage in each pixel.

Figure 23:
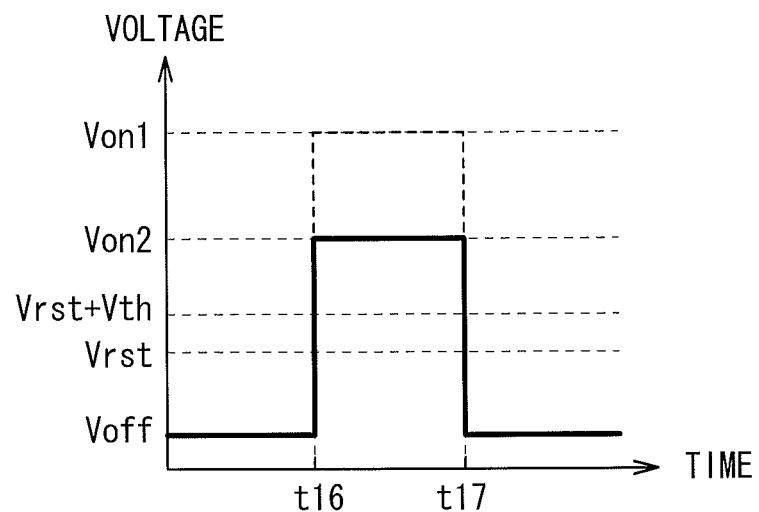
FIG. 23 is a waveform diagram illustrating voltages Von1 and Von2.

On the other hand, in the present embodiment, the transistor 22 is brought into the on-state in execution of the second resetting operation both in the first and second operational examples. In the above-mentioned case, driving as follows is executed. That is, the on-state potential Von2 which is set lower than the on-state potential Von1 is applied to the read control line Lread as illustrated in (A) of FIG. 18. In other words, driving is executed in a state that the amplitude of the potential Vread is reduced in execution of the second resetting operation. Specifically, the potential Vread is switched from the off-state potential Voff to the on-state potential Von2 at the timing t6, following which it is switched from the on-state potential Von2 to the off-state potential Voff at the timing t17. The on-state potential Von2 is a potential on the high side of the voltage pulse in the second resetting term Tr2. Although the on-state potential Von2 is lower than the on-state potential Von1 as illustrated in FIG. 23, it is set to apply a voltage which is greater than the threshold voltage Vth of the transistor 22 to the gate. Describing in more detail, a voltage which is greater than a voltage (Vrst+Vth) obtained by adding the threshold voltage Vth and the reset voltage Vrst together is applied to the gate of the transistor 22 by application of the on-state potential Von2. It is to be noted that a broken line indicates a part corresponding to a voltage waveform in execution of the first resetting operation and a solid line indicates a part corresponding to a voltage waveform in execution of the second resetting operation in FIG. 23.

It is to be noted that the on-state potential (the on-state voltage) Von1 corresponds to a specific but not limitative example of the "first voltage" in one embodiment of the present disclosure, and the on-state potential (the on-state voltage) Von2 corresponds to a specific but not limitative example of the "second voltage" in one embodiment of the present disclosure.

It is allowed to suppress charge injection which would occur with execution of the resetting operation by applying the on-state potential Von2 which is lower than the on-state voltage Von1 to the read control line Lread in execution of the second resetting operation as described above. One reason therefor lies in that generation of stored charges which is caused by the gate capacitance Cgc, the parasitic capacitance Cgd (See FIG. 21), and the like becomes difficult owing to the above. Thus, occurrence of charge injection is reduced and a fluctuation (a potential drop indicated by the arrow X1 in the example illustrated in (D) of FIG. 18) in the reset potential Vrst caused by the charge injection is reduced. That is, an offset voltage is reduced.

Further, a situation in which charge injection occurs differs with different in-plane regions in the image pickup section 11, in which the plurality of pixels 20 are arranged in arrays, for reasons as follows. That is, when the potential Vread is switched from the on-state potential to the off-state potential, a certain time is taken until the transistor 22 sufficiently shifts from the on-state to the off-state in reality. In the above-mentioned case, since the transistor 22 is substantially held in the "on-state" in a term until it sufficiently shifts from the on-state to the off-state, the photoelectric conversion device 21 is in a chargeable state. Therefore, the charge flows not to the parasitic capacitance Cgd or the like but toward the photoelectric conversion device 21 in this term.

Therefore, the more transition from the on-state to the off-state is retarded in the transistor 22, the more the charges are liable to be charged into the photoelectric conversion device 21, by which the charge injection caused by the gate capacitance Cgc, the parasitic capacitance Cgd, and the like is reduced. Since the state transition of the transistor 22 has a tendency to be gradually decelerated from an in-plane end toward a center of the image pickup section 11, the situation in which the charge injection occurs differs with different in-plane regions. Since it is allowed to reduce the offset component as mentioned above in this embodiment, an in-plane variation in the offset component is also reduced accordingly.

Since the offset component is reduced and the in-plane variation in the offset component is also reduced as mentioned above, it is allowed to narrow (minimize) a dynamic range DR used for signal storage in each pixel 20. That is, it is allowed to reduce the area for an originally undesired region which has been ensured so far in consideration of the offset component and the in-plane variation.

In the present embodiment, photoelectric conversion which is based on the incident light (the image pickup light Lin) is performed in each pixel 20 of the image pickup section 11 to execute the read driving and reset driving of the signal charges, by which the picked-up image which is based on the incident light is obtained as mentioned above. In the one-frame term, the reset driving is intermittently executed the plurality of times to apply the on-state potential Von1 to the gate of the transistor 22 in execution of the first reset driving, and then to apply the on-state potential Von2 which is lower than the on-state potential Von1 to the gate in execution of the second reset driving. Therefore, it is allowed to reduce the so-called charge injection which would occur by switching from the on-operation to the off-operation of the transistor in execution of the reset driving. Thus, noise reduction is allowed to increase image quality of the picked-up image.

It is to be noted that although description has been made by giving a case in which the reset driving is executed two times in the one-frame term as an example in the present embodiment, the present embodiment is not limited to the above. Alternatively, it may be configured to execute the reset driving three or more times in the one-frame term. In the latter case, the on-state potential Von2 which is lower than the on-state potential Von1 which has been applied, for example, firstly may be also applied in execution of any one of the second and succeeding resetting operations as in the case of the above. It is to be noted that it is preferable that it be applied in execution of the final resetting operation in the one-frame term.

Next, modification examples (Modification Examples 1 to 7) of the present embodiment will be described. It is to be noted that the same numerals are assigned to the same constitutional elements as those in the present embodiment and description thereof will be properly omitted.

Modification Example 1

Figure 24:
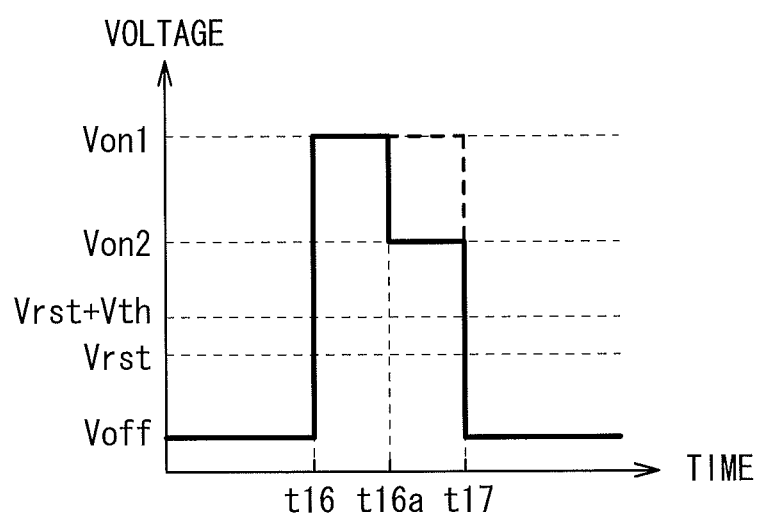
FIG. 24 is a timing waveform diagram illustrating an example of an image picking-up operation according to a modification example 1.

FIG. 24 is a timing waveform diagram illustrating an example of an image picking-up operation of the modification example 1. It may be set such that the voltage is stepwise switched (the voltage is stepwise reduced), for example, in execution of the second reset driving as illustrated in FIG. 24. In other words, the on-state potential Von2 which is lower than the on-state potential Von1 is applied in a partial term in the second resetting term Tr2. Specifically, in the second resetting term Tr2, the potential Vread is switched from the off-state potential Voff to the on-state potential Von1 at the timing t16, it is switched from the on-state potential Von1 to the on-state potential Von2 which is lower than the above at a succeeding timing 16a, and it is switched from the on-state potential Von2 to the off-state potential Voff at a further succeeding timing 16b (not illustrated in the drawing). It is to be noted that in FIG. 24, a broken line indicates a part corresponding to the voltage waveform in execution of the first resetting operation, and a solid line indicates a part corresponding to the voltage waveform in execution of the second resetting operation.

The on-state potential of the potential Vread may be stepwise reduced in execution of the second resetting operation as mentioned above, and it is also allowed to suppress occurrence of the charge injection involving the resetting operation by driving in the above-mentioned manner as in the case in the present embodiment. Thus, the same effects as those in the present embodiment are obtained also in the modification example 1.

In addition, it is allowed to shorten a resetting term (here, the second resetting term Tr2) by performing stepwise switching between the on-state potentials as in the modification example 1. That is, even when a term between the timings t16 and t16b is made shorter than the term between the timings t16 and t17 in the present embodiment, almost the same effects are obtained for reasons as follows. That is, an operation of emitting (resetting) the charges is executed basically by a discharge in the resetting term and, in addition, the discharge effect is effectively obtained by applying a higher possible voltage. On the other hand, since charge injection occurs in switching the transistor 22 from the on-operation to the off-operation as described above, it is preferable that the on-state potential before switching be low in order to reduce the charge injection. Thus, it is allowed to execute the resetting operation in a shorter time while suppressing noise generation by setting it to a relatively high voltage in a first half term (a term that hardly contributes to occurrence of the charge injection) of the resetting term and by setting it to a relatively low voltage in a second half term (a term that readily contributes to occurrence of the charge injection) of the resetting term.

It is to be noted that although the modification example 1 is configured to stepwise reduce the on-state voltage by using the two-valued (the potentials Von1 and Von2) on-state potential in execution of the second resetting operation, it is not limited to the above. Alternatively, driving may be executed by performing stepwise switching among three or more voltages of a three-valued on-state voltage.

Modification Example 2

FIG. 25 illustrates an example of a circuit configuration of a pixel (a pixel 20A) according to the modification example 2 together with a circuit configuration example of the column selecting section 17 described in the above embodiment. The pixel 20A according to the modification example 2 has a so-called passive type circuit configuration which is the same as that of the pixel 20 according to the present embodiment, and includes one photoelectric conversion device 21 and one transistor 22. The read control line Lread extending in the H direction and the signal line Lsig extending in the V direction are connected to the pixel 20A.

However, in the pixel 20A according to the modification example 2, the anode of the photoelectric conversion device 21 is connected to the storage node N and the cathode thereof is connected to a power source, unlike the pixel 20 according to the present embodiment. The storage node N may be connected to the anode of the photoelectric conversion device 21 in the pixel 20A as described above, and the same effects as those of the image pickup unit 1 according to the present embodiment are obtained even when it is configured as mentioned above.

Modification Example 3

Figure 26:
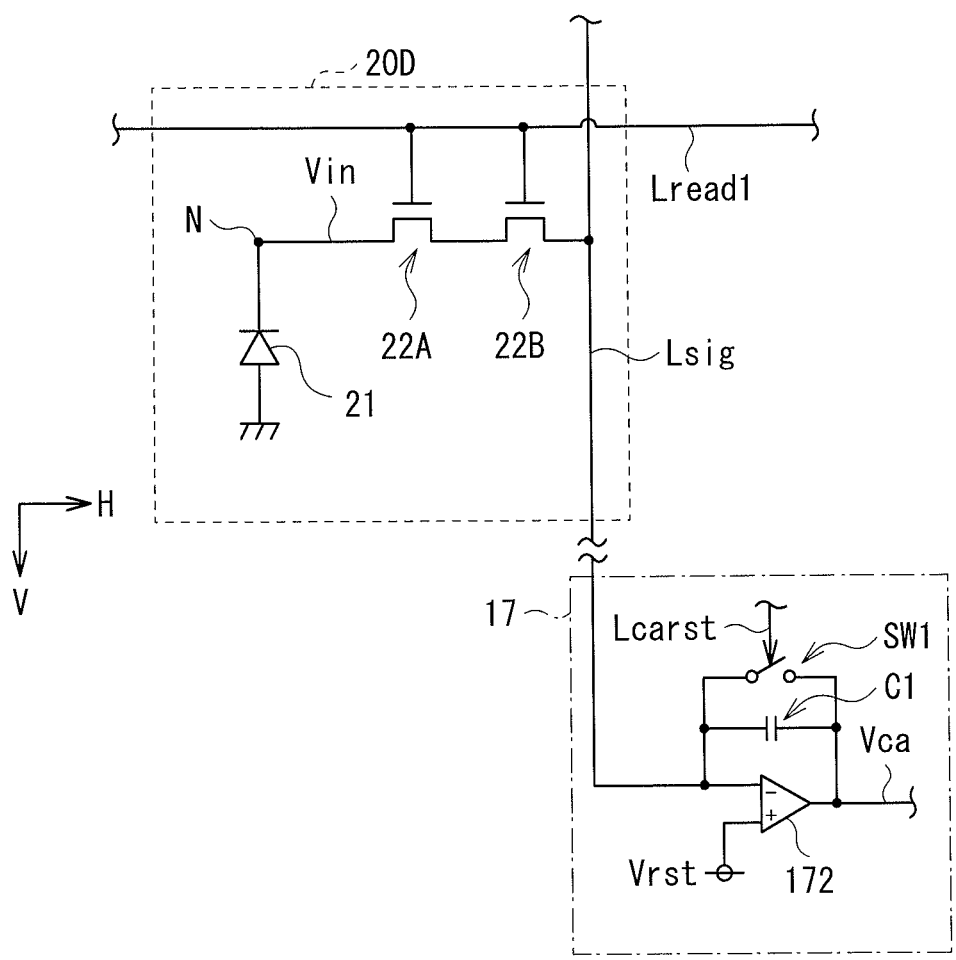
FIG. 26 is a circuit diagram illustrating a configuration example of a pixel and the like according to a modification example 3.

FIG. 26 illustrates an example of a circuit configuration of a pixel (a pixel 20D) according to the modification example 3 together with a circuit configuration example of the column selecting section 17 described in the above embodiment. The pixel 20D according to the modification example 3 has a so-called passive type circuit configuration which is the same as that of the pixel 20 according to the present embodiment, includes one photoelectric conversion device 21, and is connected to the read control line Lread extending in the H direction and the signal line Lsig extending in the V direction.

However, the pixel 20D according to the modification example 3 includes two transistors (transistors 22A and 22B). The transistors 22A and 22B are connected in series with each other (a source or a drain of one transistor is electrically connected to a source or a drain of the other transistor). In addition, each gate of each of the transistors 22A and 22B is connected to the read control line Lread.

The transistors 22A and 22B which are connected in series with each other may be disposed in the pixel 20D as mentioned above. In the above-mentioned case, it is also allowed to suppress the fluctuation in the potential Vn induced by charge injection by executing such read driving and reset driving as described in the above embodiment.

Modification Examples 4 and 5

Figure 27:
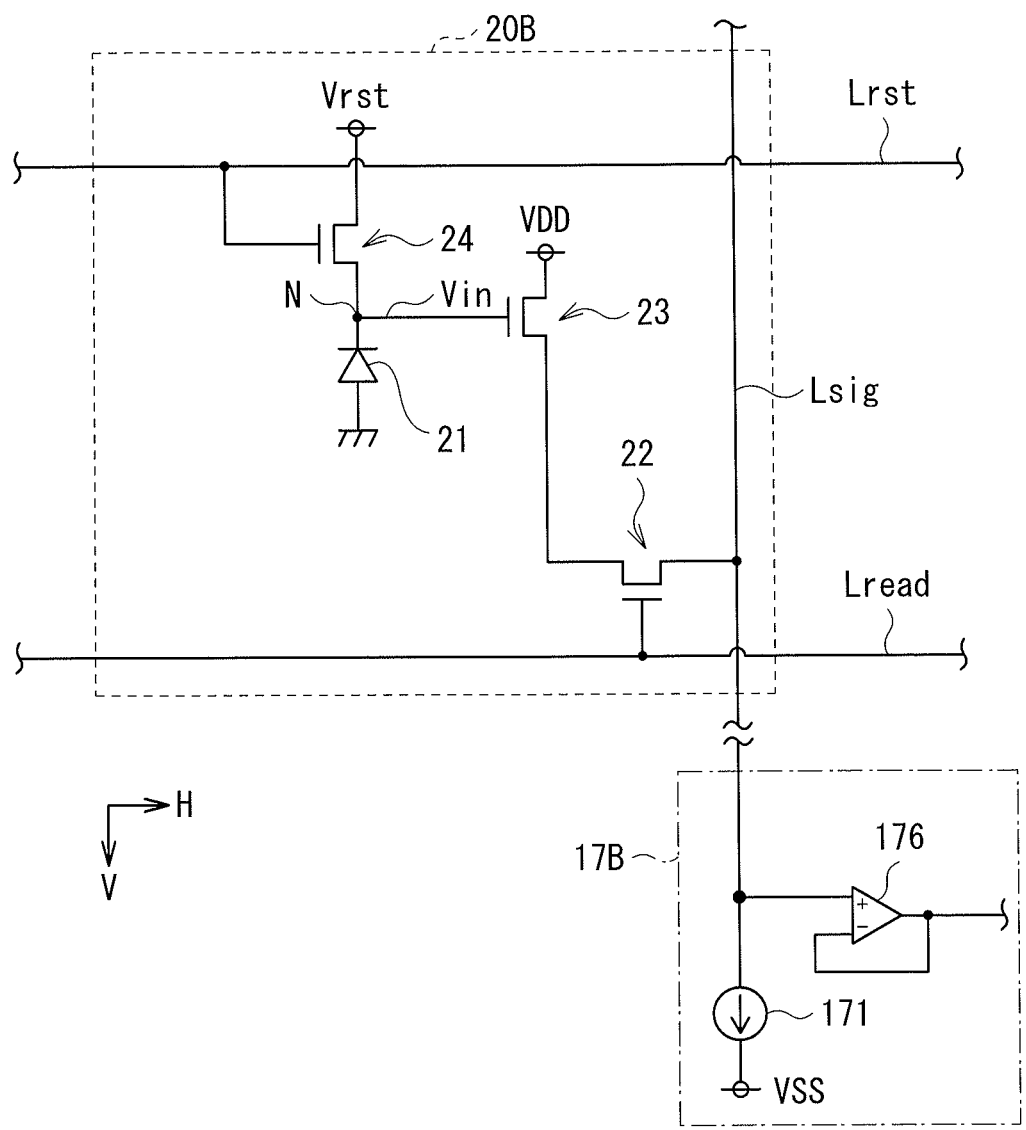
FIG. 27 is a circuit diagram illustrating a configuration example of a pixel and the like according to a modification example 4.
Figure 28:
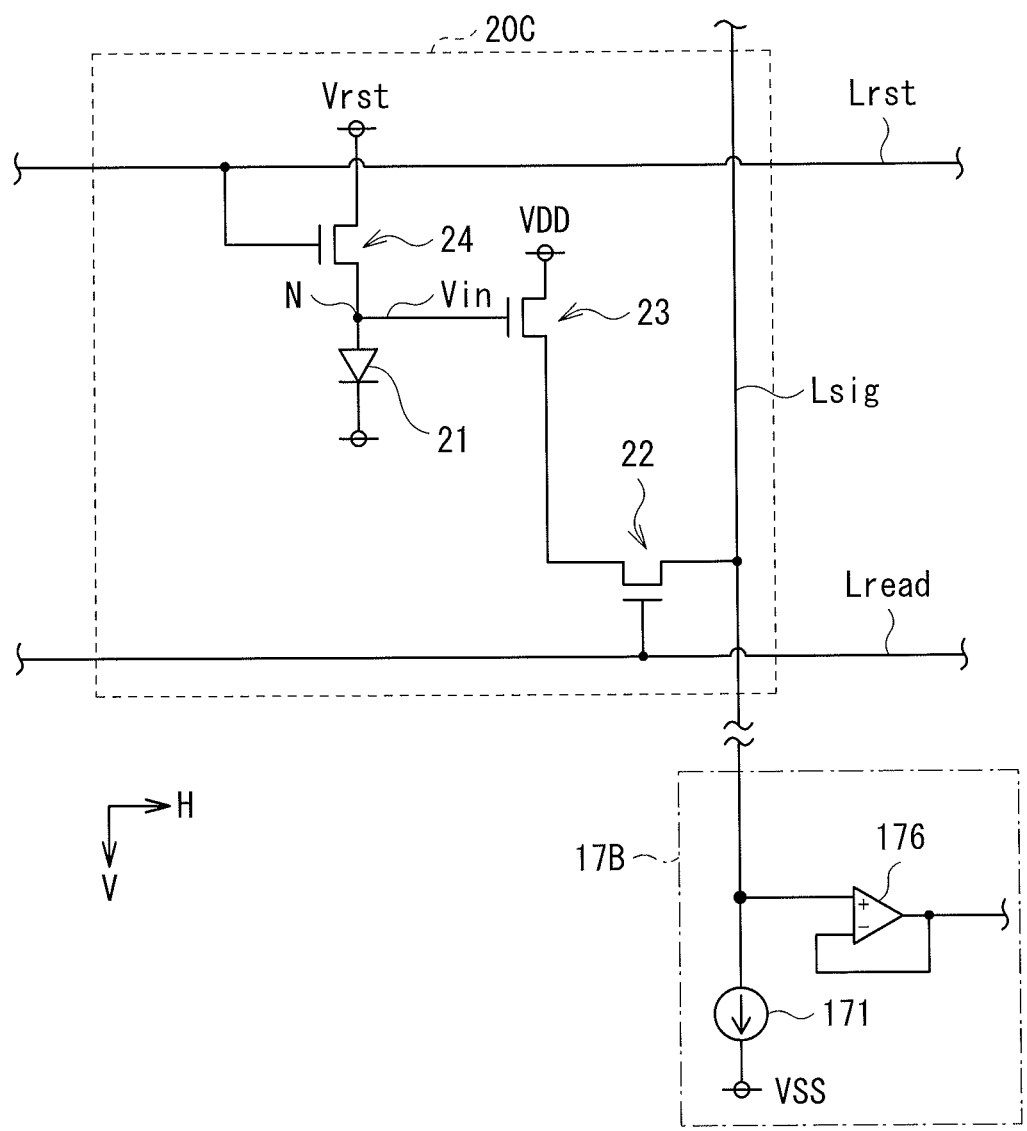
FIG. 28 is a circuit diagram illustrating a configuration example of a pixel and the like according to a modification example 5.

FIG. 27 illustrates an example of a circuit configuration of a pixel (a pixel 20B) according to the modification example 4 together with a circuit configuration example of a column selecting section 17B which will be described hereinbelow. FIG. 28 illustrates an example of a circuit configuration of a pixel (a pixel 20C) according to the modification example 5 together with a circuit configuration example of the column selecting section 17B. Each of the pixels 20B and 20C according to the modification examples 4 and 5 includes a so-called an active type pixel circuit, unlike the pixels 20 and 20A described so far.

Each of the active type pixels 20B and 20C includes one photoelectric conversion device 21 and three transistors 22, 23, and 24. The read control line Lread (that is, read control lines Lread1 and Lread2 which are not illustrated in the drawings) and a reset control line Lrst extending in the H direction and the signal line Lsig extending in the V direction are connected to each of the pixels 20B and 20C.

In each of the pixels 20B and 20C, one gate of the transistor 22 is connected to the read control line Lread1, the other gate thereof is connected to the read control line Lread2, the source thereof is connected to the signal line Lsig, and the drain thereof is connected to a drain of the transistor 23 that configures a source follower circuit. A source of the transistor 23 is connected to a power source VDD, and a gate thereof is connected to the cathode (the example in FIG. 27) or the anode (the example in FIG. 28) of the photoelectric conversion device 21 and to a drain of the transistor 24 that functions as a reset transistor via the storage node N. A gate of the transistor 24 is connected to the reset control line Lrst so as to apply the reset voltage Vrst to a source thereof. In the modification example 4 in FIG. 27, the anode of the photoelectric conversion device 21 is connected to ground (grounded), and in the modification example 5 in FIG. 28, the cathode of the photoelectric conversion device 21 is connected to the power source.

In addition, in the modification examples 4 and 5, the column selecting section 17B includes a constant current source 171 and an amplifier 176 in place of the charge amplifier 172, the capacitative element C1, and the switch SW1 included in the above-mentioned column selecting section 17. In the amplifier 176, the signal line Lsig is connected to a positive input terminal, and a negative input terminal and an output terminal are mutually connected to form a voltage follower circuit. It is to be noted that one terminal of the constant current source 171 is connected to a first end side of the signal line Lsig, and a power source VSS is connected to the other terminal of the constant current source 171.

The potential Vn of the storage node N fluctuates (for example, drops) by charge injection which would occur with execution of the resetting operation even in the image pickup unit that includes the pixel 20B or 20C having an active circuit configuration as mentioned above. Thus, it is allowed to reduce the charge injection by executing the reset driving by using a predetermined on-state voltage as in the case in the above-mentioned embodiment, so as to increase image quality of the picked-up image also in the modification examples 4 and 5. However, the image picking-up operation (line sequential image pickup driving) is executed as follows on the pixels 20B and 20C having the active type circuit configuration each.

Figure 29:
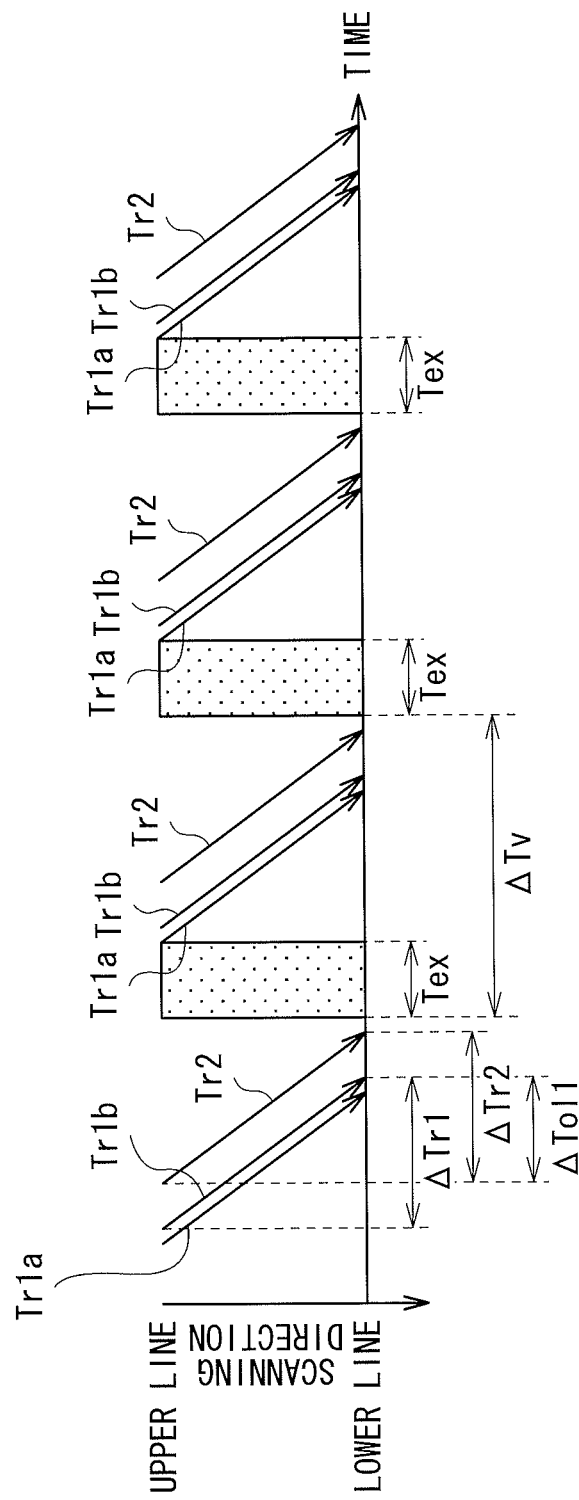
FIG. 29 is a timing chart illustrating an example of a line-sequential image picking-up operation in an active type pixel circuit.

That is, line sequential read driving and plural-time (here, two-time) line sequential reset driving are executed independently of one another (intermittently), for example, as illustrated in FIG. 29. Specifically, the line sequential read driving for executing a line sequential operation in a reading term Tr1a, the first line sequential reset driving for executing a line sequential operation in a first-time resetting term (a first resetting term Tr1b), and the second line sequential reset driving for executing a line sequential operation in a second-time resetting term (a second resetting term Tr2) are executed independently of one another. It is to be noted that in case of the active type circuit configuration, each resetting operation is executed by bringing the transistor 24 as a reset transistor into the on-state.

Modification Examples 6 and 7

Figure 30A:
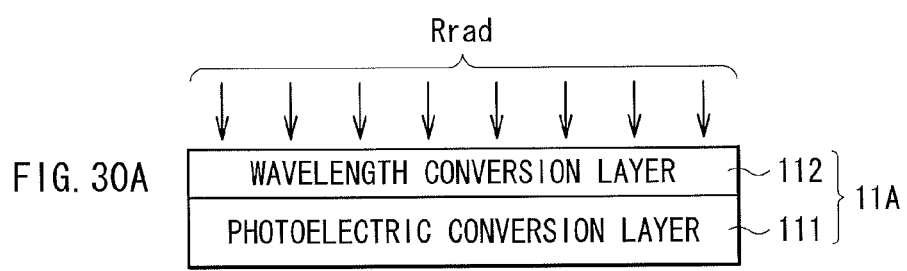
FIG. 30A is a schematic diagram illustrating a rough configuration example of an image pickup section according to a modification example 6.
Figure 30B:
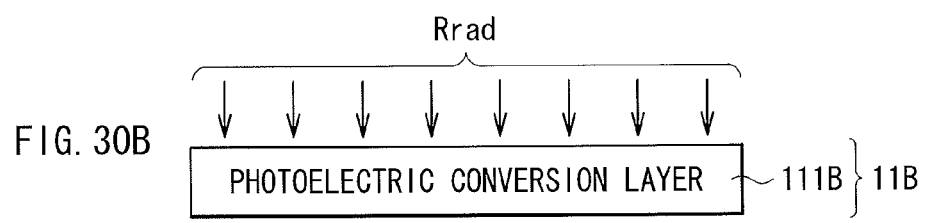
FIG. 30B is a schematic diagram illustrating a rough configuration example of an image pickup section according to a modification example 7.

FIG. 30A and FIG. 30B schematically illustrate rough configuration examples of image pickup sections (image pickup sections 11A and 11B) according to the modification examples 6 and 7.

The image pickup section 11A according to the modification example 6 illustrated in FIG. 30A further includes a wavelength conversion layer 112 disposed on the photoelectric conversion layer 111 (the light receiving surface side) which has been described in the present embodiment. The wavelength conversion layer 112 converts the wavelength of a radioactive ray Rrad (an α ray, a β ray, a γ ray, an X-ray, and the like) so as to be within a sensitive range of the photoelectric conversion layer 111, by which the photoelectric conversion layer 111 is allowed to read information which is based on the radioactive ray Rrad. The wavelength conversion layer 112 includes a phosphor (for example, a scintillator) that converts a radioactive ray such as, for example, an X-ray or the like into visible light. The wavelength conversion layer 112 is obtained, for example, by forming an organic flattened film such as a flattened film made of, for example, a spin-on glass material or the like, on an upper part of the photoelectric conversion layer 111, and forming a phosphor film with CsI, NaI, $CaF_2$, or the like thereon. The image pickup section 11A is applied to, for example, a so-called indirect radioactive-ray image pickup unit.

The image pickup section 11B according to the modification example 7 illustrated in FIG. 30B includes a photoelectric conversion layer 111B that converts the incident radioactive ray Rrad into an electric signal, unlike the image pickup section according to the embodiment. The photoelectric conversion layer 111B is made of, for example, an amorphous selenium (a-Se) semiconductor, a cadmium telluride (CdTe) semiconductor, or the like. The image pickup section 11B is applied to, for example, a so-called direct radioactive-ray image pickup unit.

The image pickup units respectively including the image pickup sections 11A and 11B according to the modification examples 6 and 7 are utilized as various kinds of radioactive-ray image pickup units, each being configured to obtain the electric signal on the basis of the incident radioactive ray Rrad. It is applicable to, for example but not limited to, a medical X-ray image pickup unit (such as a digital radiography or the like), X-ray equipment for hand baggage search which is used in an airport or the like, industrial X-ray image pickup units (for example, an unit for examining dangerous goods in containers and an unit for examining the contents in bags), and the like, when utilized as a radioactive-ray image pickup unit.

Application Example

Then, each of the image pickup units according to the embodiment and the respective modification examples (the modification examples 1 to 7) is applicable to such an image pickup display system as described hereinbelow.

Figure 31:
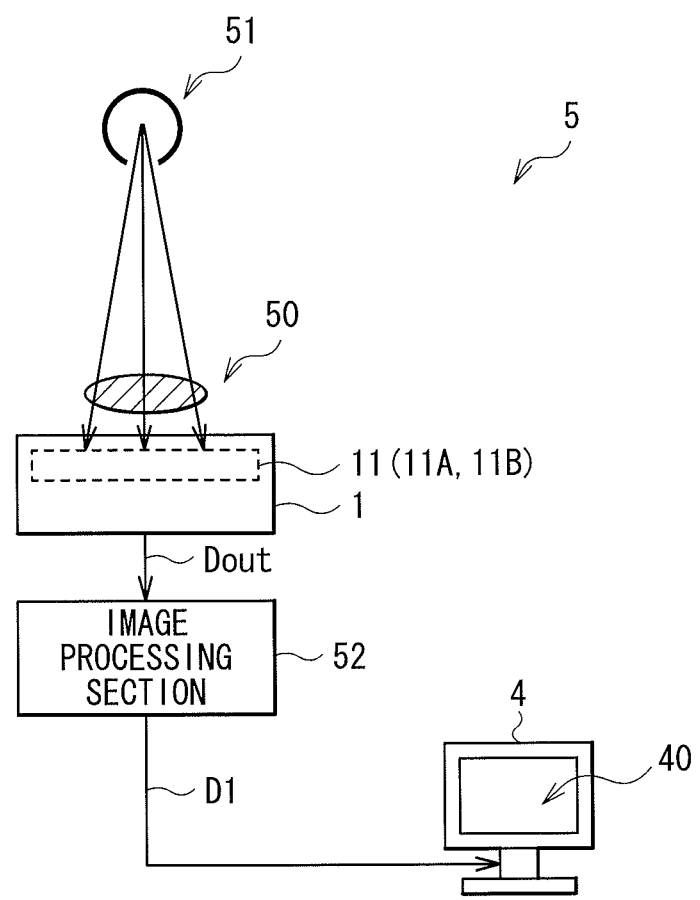
FIG. 31 is a schematic diagram illustrating a rough configuration example of an image pickup display system according to an application example.

FIG. 31 is a schematic diagram illustrating a schematic configuration example of an image pickup display system (an image pickup display system 5) according to an application example. The image pickup display system 5 includes the image pickup unit 1 that includes the image pickup section 11 (or 11A or 11B) or the like according to the embodiment or the like, an image processing section 52, and a display 4, and is configured as an image pickup display system using a radioactive ray (a radioactive ray image pickup display system) in this example.

The image processing section 52 generates image data D1 by performing predetermined image processing on image data Dout (an image pickup signal) which is output from the image pickup unit 1. The display 4 displays an image which is based on the image data D1 so generated by the image processing section 52 on a predetermined monitor screen 40.

In the image pickup display system 5, the image pickup unit 1 (here, a radioactive ray image pickup unit) acquires the image data Dout of an object 50 on the basis of irradiation light (here, a radioactive ray) that irradiates the object 50 from a light source (here, a radioactive ray source such as an X-ray source or the like) and outputs it to the image processing section 52. The image processing section 52 performs the above-mentioned predetermined image processing on the input image data Dout, and outputs the image-processed image data (display data) D1 to the display 4. The display 4 displays image information (a picked-up image) on the monitor screen 40 on the basis of the input image data D1.

Since, in the image pickup display system according to the application example, the image of the object 50 is acquired as an electric signal in the image pickup unit 1 as described above, image display is allowed by transmitting the acquired electric signal to the display 4. That is, observation of the image of the object 50 is allowed without using an ever-used radiographic film, and it is also allowed to cope with moving image capturing and moving image display.

It is to be noted that although description has been made by giving a case in which the image pickup unit 1 is configured as a radioactive ray image pickup unit so as to be applicable to an image pickup display system using a radioactive ray as an example in this application example, the image pickup display system according to the application example of the present disclosure is also applicable to a system using an image pickup unit of the type other than the above.

Although the embodiment, the modification examples, and the application example of the present disclosure have been given as described above, the contents of the present disclosure are not limited to the above-mentioned embodiment and the examples and may be modified in a variety of ways. For example, the circuit configuration of the pixel in the image pickup section is not limited to those (the circuit configurations of the pixels 20, and 20A to 20D) described in the above-mentioned embodiment and examples, and the pixel may have other circuit configurations. In addition, the circuit configurations of the row scanning section, the column selecting section, and the like are not limited to those described in the above-mentioned embodiment and examples, and these sections may have other circuit configurations similarly.

In addition, the passive type and active type ones have been illustrated as examples of the circuit configurations of the pixel in the above-mentioned embodiment and examples. When the active type one is used, the reading operation and the resetting operations are executed independently of one another as described above. Therefore, the on-state voltage may be set to a lower potential or may be changed stepwise even in the resetting operation (the first resetting operation) executed just after execution of the reading operation.

Further, the image pickup section, the row scanning section, the A/D converting section (the column selecting section), the column scanning section, and the like which have been described in the embodiment and examples may be formed, for example, on the same substrate. Specifically, it is also allowed to form switches and the like in the circuit parts of the above-mentioned sections on the same substrate by using, for example, a polycrystalline semiconductor made of low-temperature polycrystalline silicon and the like. Thus, it is allowed to execute driving operations on the same substrate on the basis of control signals from, for example, an externally-installed system control section, and hence it is allowed to improve reliability in frame narrowing (a frame structure with three free sides) and wiring connection.

Accordingly, it is possible to achieve at least the following configurations from the above-described example embodiments and the modifications of the disclosure.

(1) An image pickup unit, including:
an image pickup section having a plurality of pixels, each of the pixels including a photoelectric conversion device and a field effect transistor; and
a driving section, by using the transistor, executing read driving and reset driving on a signal charge stored in the pixel, the driving section intermittently executing the reset driving a plurality of times in a one-frame term, and executing on-operation of the transistor by applying, to the transistor over at least one resetting term in the one-frame term or over a partial term in the at least one resetting term, a second voltage that is lower than a first voltage applied in a resetting term in the one-frame term other than the at least one resetting term.

(2) The image pickup unit according to (1), wherein the driving section applies the second voltage to the transistor at least in execution of final reset driving.

(3) The image pickup unit according to (1) or (2), wherein the driving section sets the second voltage to be stepwise reduced in time series.

(4) The image pickup unit according to (3), wherein a term during which the second voltage is being applied is shorter than a term during which the first voltage is being applied.

(5) The image pickup unit according to any one of (1) to (4), wherein the second voltage is greater than a threshold voltage of the transistor.

(6) The image pickup unit according to any one of (1) to (5), wherein the driving section executes first reset driving in the one-frame term using the first voltage with the execution of the read driving, and uses the second voltage in execution of final reset driving.

(7) The image pickup unit according to any one of (1) to (6), wherein the photoelectric conversion device is one of a positive-intrinsic-negative (PIN) type photodiode and a metal-insulator-semiconductor (MIS) type sensor.

(8) The image pickup unit according to any one of (1) to (7), wherein the image pickup section generates an electric signal based on an incident radioactive ray.

(9) The image pickup unit according to (8), wherein the image pickup section includes, on the photoelectric conversion device, a wavelength conversion layer that converts a wavelength of the radioactive ray to allow the wavelength to be within a sensitive range of the photoelectric conversion device.

(10) The image pickup unit according to (9), wherein the radioactive ray is an X-ray.

(11) The image pickup unit according to any one of (1) to (10), wherein a semiconductor layer of the transistor is made of one of amorphous silicon, polycrystalline silicon, microcrystalline silicon, and an oxide semiconductor.

(12) An image pickup display system with an image pickup unit and a display that displays an image based on an image pickup signal obtained from the image pickup unit, the image pickup unit including:

an image pickup section having a plurality of pixels, each of the pixels including a photoelectric conversion device and a field effect transistor; and a driving section, by using the transistor, executing read driving and reset driving on a signal charge stored in the pixel, the driving section intermittently executing the reset driving a plurality of times in a one-frame term, and executing on-operation of the transistor by applying, to the transistor over at least one resetting term in the one-frame term or over a partial term in the at least one resetting term, a second voltage that is lower than a first voltage applied in a resetting term in the one-frame term other than the at least one resetting term.

It is to be noted that any combinations of (2) to (11) directed to the image pickup unit are applicable to (12) directed to the image pickup display system unless any contradictions occur. Such combinations are also considered as preferred combinations of embodiments according to the technology.

The disclosure contains subject matter related to that disclosed in Japanese Priority Patent Application JP 2011-229996 filed in the Japan Patent Office on Oct. 19, 2011, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An image pickup unit, comprising:
an image pickup section having a plurality of pixels, each of the pixels including a photoelectric conversion device and a field effect transistor; and
a driving section configured to apply, during a first term, a first voltage to the transistor to execute read driving and reset driving on a signal charge stored in the pixel, the driving section further configured to execute the reset driving a plurality of times in a one-frame term by applying a second voltage to the transistor during at least one second term following the first term, wherein the second voltage is lower than the first voltage,
wherein the driving section is further configured to set the second voltage to be stepwise reduced in time series during the at least one second term.

2. The image pickup unit according to claim 1, wherein the driving section is configured to apply the second voltage to the transistor at least in execution of final reset driving.

3. The image pickup unit according to claim 1, wherein the at least one second term is shorter than the first term.

4. The image pickup unit according to claim 1, wherein the second voltage is greater than a threshold voltage of the transistor.

5. The image pickup unit according to claim 1, wherein the driving section is further configured to use the first voltage to execute first reset driving and the read driving at the same time during the first term and use the second voltage in execution of final reset driving.

6. The image pickup unit according to claim 1, wherein the photoelectric conversion device is one of a positive-intrinsic-negative (PIN) type photodiode and a metal-insulator-semiconductor (MIS) type sensor.

7. The image pickup unit according to claim 1, wherein the image pickup section is configured to generate an electric signal based on an incident radioactive ray.

8. The image pickup unit according to claim 7, wherein the image pickup section includes, on the photoelectric conversion device, a wavelength conversion layer that converts a wavelength of the radioactive ray to allow the wavelength to be within a sensitive range of the photoelectric conversion device.

9. The image pickup unit according to claim 8, wherein the radioactive ray is an X-ray.

10. The image pickup unit according to claim 1, wherein a semiconductor layer of the transistor is made of one of amorphous silicon, polycrystalline silicon, microcrystalline silicon, and an oxide semiconductor.

11. An image pickup display system with an image pickup unit and a display that displays an image based on an image pickup signal obtained from the image pickup unit, the image pickup unit comprising:
an image pickup section having a plurality of pixels, each of the pixels including a photoelectric conversion device and a field effect transistor; and
a driving section configured to apply, during a first term, a first voltage to the transistor to execute read driving and reset driving on a signal charge stored in the pixel, the driving section further configured to execute the reset driving a plurality of times in a one-frame term by applying a second voltage to the transistor during at least one second term following the first term, wherein the second voltage is lower than the first voltage, wherein the driving section is further configured to set the second voltage to be stepwise reduced in time series during the at least one second term.

12. The image pickup unit according to claim 1, wherein each of the pixels comprises a passive-type pixel circuit.

* * * * *